US005869686A

United States Patent [19]

Dorfmeister et al.

[11] Patent Number: 5,869,686

[45] Date of Patent: Feb. 9, 1999

[54] SUBSTITUTED PYRAZOLE DERIVATIVES, PROCESSES FOR THEIR PREPARATION AND THEIR USE AS HERBICIDES

[75] Inventors: Gabriele Dorfmeister; Helga Franke; Jens Geisler; Uwe Hartfiel; Jürgen Bohner; Richard Rees, all of Berlin, Germany

[73] Assignee: Hoechst Schering AgrEvo GmbH, Berlin, Germany

[21] Appl. No.: 58,033

[22] Filed: Apr. 10, 1998

Related U.S. Application Data

[62] Division of Ser. No. 416,748, Jun. 1, 1995, Pat. No. 5,756,424.

[30] Foreign Application Priority Data

| | | | |
|---|---|---|---|
| Oct. 12, 1992 | [DE] | Germany | 42 34 709.2 |
| Mar. 24, 1993 | [DE] | Germany | 43 10 091.0 |
| May 3, 1993 | [DE] | Germany | 43 15 330.5 |

[51] Int. Cl.$^6$ ........................ A01N 43/56; C07D 231/38; C07D 231/40

[52] U.S. Cl. ........................ 548/365.4; 504/282; 544/140

[58] Field of Search .......................... 548/365.4; 504/282

[56] References Cited

U.S. PATENT DOCUMENTS 5,405,829 4/1995 Hartfiel et al. ........................ 548/365.4

*Primary Examiner*—Robert W. Ramsuer
*Attorney, Agent, or Firm*—Ostrolenk, Faber, Gerb & Soffen, LLP

[57] ABSTRACT

New substituted pyrazole derivatives of general formula I are described

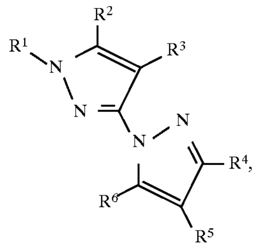

(I)

in which $R^1$, $R^2$, $R^3$, $R^4$, $R^5$ and $R^6$ have the meanings given in the description, processes for their preparation, as well as intermediates, and their use as herbicides.

21 Claims, No Drawings

SUBSTITUTED PYRAZOLE DERIVATIVES, PROCESSES FOR THEIR PREPARATION AND THEIR USE AS HERBICIDES

This is a divisional of application Ser. No. 08/416,748, filed Jun. 1, 1995 now U.S. Pat. No. 5,756,424.

FIELD OF THE INVENTION

This invention relates to new substituted pyrazole derivatives, their preparation, as well as intermediates, and their use as herbicides.

PRIOR ART

It is known that 1-phenylpyrazoles possess herbicidal activism (EP 154115).

However the herbicidal activity of these compounds in not high enough or selectivity problems can occur in important crops.

The object of the present invention is to make new compounds that have improved biological properties over the known compounds.

It has now been found that substituted pyrazole derivatives of general formula I

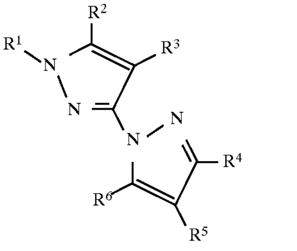

(I)

in which $R^1$ is $C_1$–$C_4$-alkyl;

$R^2$ is $C_1$–$C_4$-alkyl, $C_1$–$C_4$-alkylthio, $C_1$–$C_4$-alkoxy, each of which is optionally substituted by one or more halogen atoms, or $R^1$ and $R^2$ together form the group —$(CH_2)_m$—;

$R^3$ is hydrogen or halogen, $R^4$ is hydrogen or $C_1$–$C_4$-alkyl, $R^5$ is hydrogen, nitro, cyano or the groups —$COOR^7$, —C(=X)$NR^8R^4$ or —C(=X)$R^{10}$, $R^6$ is hydrogen, halogen, cyano, $C_1$–$C_4$-alkyl, (optionally substituted by one or more halogen or hydroxy groups), $C_1$–$C_4$-alkoxy, phenyl, (optionally substituted by one or more halogen, nitro, cyano, $C_1$–$C_4$-alkyl, $C_1$–$C_4$-alkoxy or halo-$C_1$–$C_4$-alkyl groups), pyrrolyl, or is a $C_2$–$C_8$-alkyl, $C_3$–$C_8$-alkenyl, $C_3$–$C_8$-alkynyl or $C_3$–$C_8$-alkoxy group, each of which is interrupted by one or more oxygen atoms, or is the group: $NR^{11}R^{12}$

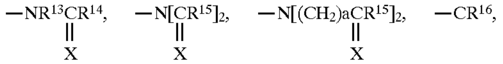

—S(O)$_n$R$^{17}$,

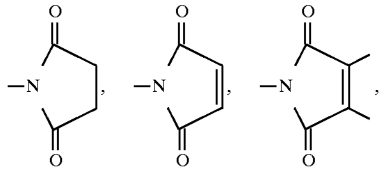

-continued

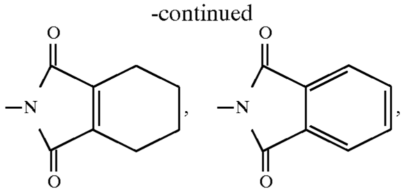

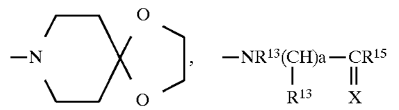

—$(CH_2)_a$—A, —$(CH_2)_a$—O—$(CH_2)_b$-$R^{22}$, —$(CH_2)_a$—O-$R^{23}$ or —$COR^{24}$, $R^7$, $R^8$ and $R^9$, which may be the same or different, are hydrogen or $C_1$–$C_4$-alkyl or $R^8$ and $R^9$ together with the nitrogen to which they are attached form a 5 or 6 membered saturated carbocyclic ring;

$R^{10}$ is hydrogen or $C_1$–$C_4$-alkyl, optionally substituted by one or more halogen atoms, $R^{11}$ is hydrogen, $C_1$–$C_4$-alkyl, $C_2$–$C_6$-alkenyl, $C_3$–$C_6$-alkynyl or phenyl (each of which is optionally substituted by one or more halogen atoms), $C_3$–$C_8$-cycloalkyl, cyanomethyl or the group $R^{21}$CO—;

$R^{12}$ is $C_1$–$C_6$-alkyl, $C_2$–$C_6$-alkenyl, $C_3$–$C_6$-alkynyl or phenyl (each of which is optionally substituted by one or more halogen atoms), $C_3$–$C_8$-cycloalkyl, cyanomethyl, $C_1$–$C_4$-alkoxy-$C_1$–$C_6$-alkyl, di-$C_1$–$C_4$-alkylamino-$C_1$–$C_4$-alkyl, tetrahydrofurfurylmethyl, $C_3$–$C_6$-alkynyloxy-$C_1$–$C_4$-alkyl, benzyl, (optionally substituted by one or more halogen, nitro, cyano, $C_1$–$C_4$-alkyl, $C_1$–$C_4$-alkoxy or halo-$C_1$–$C_4$-alkyl groups), or is the group —C(=X)$R^{21}$, —$(CH_2)_a$—$(O)_d$-$R^{28}$, —$(CH_2)_a$—O—$(CH_2)_b$-$R^{28}$ or —$(CH_2)_a$—X-$R^{34}$, and when $R^5$ is —C(=O)$R^{10}$, and/or when $R^1$ is $C_1$–$C_4$-alkyl, $R^2$ is difluoromethoxy, $R^3$ is bromo and $R^5$ is nitro or cyano, $R^{12}$ can also be hydrogen; or $R^{11}$ and $R^{12}$ together with the nitrogen to which they are attached form a 3, 5 or 6 membered saturated carbocyclic or aromatic ring, in which a carbon atom is optionally substituted by an oxygen atom;

$R^{13}$ is hydrogen, $C_1$–$C_4$-alkyl, $C_2$–$C_6$-alkenyl or $C_3$–$C_6$-alkynyl; or $R^{13}$ and $R^{14}$ together form the group —$(CH_2)_p$—;

$R^{14}$ and $R^{15}$, which may be the same or different, are $C_1$–$C_4$-alkyl, $C_2$–$C_6$-alkenyl, $C_3$–$C_6$-alkynyl or phenyl (each of which is optionally substituted by one or more halogen atoms), hydrogen, $C_3$–$C_6$-cycloalkyl or the groups —$XR^{18}$ or —$NR^{19}R^{20}$;

$R^{16}$ is hydrogen, $C_1$–$C_6$-alkyl, $C_2$–$C_6$-alkenyl, $C_3$–$C_6$-alkynyl, $C_1$–$C_4$-alkylcarbonyl, cyano-$C_1$–$C_3$-alkyl, $C_1$–$C_4$-alkoxycarbonyl-$C_1$–$C_4$-alkyl, di-$C_1$–$C_4$-alkoxycarbonyl-$C_1$–$C_4$-alkyl, benzyl, $C_1$–$C_4$-alkoxy-$C_3$–$C_8$-alkynyl, or the group —$(CH_2)_a$-$R^{33}$, —$(CH_2)_a$—X-$R^{30}$, —$(CH_2)_a$—X—$(CH_2)_b$-$R^{30}$ or —$(CH_2)_a$—X—$(CH_2)_b$—X—$(CH_2)_c$-$R^{30}$, $R^{17}$ is hydrogen, $C_1$–$C_4$-alkyl, $C_2$–$C_6$-alkenyl, $C_3$–$C_6$-alkynyl, cyano-$C_1$–$C_3$-alkyl, $C_1$–$C_4$-alkylcarbonyl-$C_1$–$C_3$-alkyl or phenyl, $R^{18}$ is $C_1$–$C_4$-alkyl, optionally substituted by one or more halogens;

$R^{19}$ and $R^{20}$, which may be the same or different, are hydrogen or $C_1$–$C_4$-alkyl;

$R^{21}$ is $C_1$–$C_4$-alkyl, (optionally substituted by one or more halogens), $C_1$–$C_4$-alkoxy-$C_1$–$C_4$-alkyl, $C_1$–$C_4$-alkylthio-$C_1$–$C_4$-alkyl, $C_3$–$C_6$cycloalkyl, phenyl, (optionally substituted by one or more halogen, nitro, cyano, $C_1$–$C_4$-alkyl, $C_1$–$C_4$-alkoxy or halo-$C_1$–$C_4$-alkyl groups), or is the group —$NR^{31}R^{32}$ or —$(CH_2)_a$—$(O)_d$-$R^{33}$;

$R^{22}$ is $C_1$–$C_4$-alkoxycarbonyl or carboxy, $R^{23}$ is chloromethyl, cyanomethyl, $C_3$–$C_6$-cycloalkyl (optionally interrupted by one or more oxygen atoms), or $C_1$–$C_4$-alkoxycarbonyl-$C_1$–$C_4$-alkyl, $R^{24}$ is hydroxy or the group —$NR^{25}R^{26}$;

A is —$NR^{25}R^{26}$ or —$S(O)_n$-$R^{27}$;

$R^{25}$ and $R^{26}$, which may be the same or different, are hydrogen or $C_1$–$C_4$-alkyl;

$R^{27}$ is $C_1$–$C_4$-alkyl, $C_1$–$C_4$-alkoxycarbonyl-$C_1$–$C_4$-alkyl or carboxy, $R^{28}$ is hydrogen, hydroxy, halogen, $C_1$–$C_4$-alkyl, (optionally substituted by one or more $C_1$–$C_4$-alkoxy groups), $C_3$–$C_6$-cycloalkyl (optionally interrupted by one or more oxygen atoms and optionally substituted by dimethyl), furyl, thienyl or —C(═O)$R^{29}$;

$R^{29}$ and $R^{30}$, which may be the same or different, are $C_1$–$C_4$-alkyl or $C_1$–$C_4$-alkoxy;

$R^{31}$ and $R^{32}$, which may be the same or different, are $C_1$–$C_4$-alkyl or phenyl;

$R^{33}$ is $C_3$–$C_6$-cycloalkyl (optionally interrupted by one or more oxygen atoms and optionally substituted by dimethyl), furyl, thienyl or —C(═O)$R^{29}$;

$R^{34}$ is $C_1$–$C_4$-alkyl;

a, b and c are 1, 2 or 3;

d is 0 or 1;

m is 3 or 4;

p is 2 or 3; and

X is oxygen or sulfur, possess better herbicide properties than the known compounds of related structure.

Particularly active are those pyrazole derivatives as defined above, in which $R^1$ is methyl;

$R^2$ is methylthio or difluoromethoxy (and especially difluoromethoxy); or $R^1$ and $R^2$ together form the group —$(CH_2)_4$;

$R^3$ is hydrogen, chloro or bromo;

$R^4$ is hydrogen;

$R^5$ is hydrogen, nitro, cyano or —C(═X)$R^{10}$.

In a particularly preferred group of compounds, $R^6$ is hydrogen, halogen, cyano, $C_1$–$C_4$-alkyl, $C_{1-4}$-alkylthio or —$NR^{11}R^{12}$, with $R^{11}$ and $R^{12}$ preferably being hydrogen, $C_{1-4}$-alkyl or $C_{1-4}$-alkoxycarbonyl.

The term "halogen" means fluorine, chlorine, bromine and iodine.

It is to be understood that the term "alkyl", "alkenyl" and "alkynyl" includes branched as well as straight chained hydrocarbon groups.

The invention also includes intermediates of general formula II

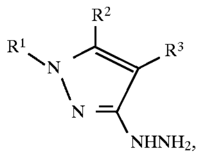

(II)

in which $R^1$, $R^2$ and $R^3$ have the meanings given in general formula I, intermediates of general formula Ii

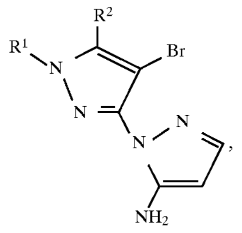

(Ii)

in which $R^1$ and $R^2$ have the meanings given in general formula I, intermediates of general formula Ij

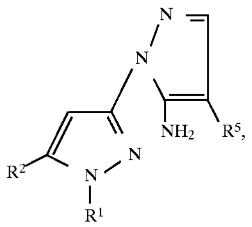

(Ij)

in which $R^1$, $R^2$ and $R^5$ have the meanings given in general formula I, intermediates of general formula Ik

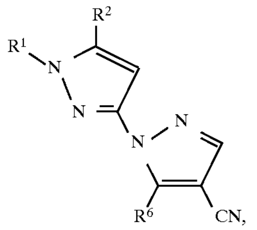

(Ik)

in which $R^1$, $R^2$ and $R^6$ have the meanings given in general formula I, intermediates of general formula Il

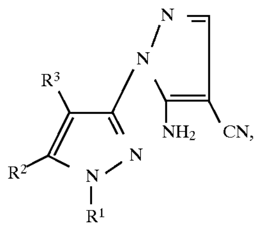

(Il)

in which $R^1$, $R^2$ and $R^3$ have the meanings given in general formula I, and intermediates of general formula Im

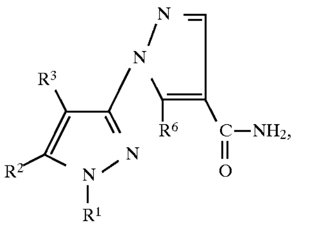

(Im)

in which $R^1$, $R^2$, $R^3$ and $R^6$ have the meanings given in general formula I.

The compounds of the invention of general formula I can be prepared, by a process in which A) a compound of general formula II

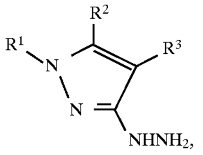

(II)

in which $R^1$, $R^2$ and $R^3$ have the meanings given in general formula I, is reacted with a compound of general formula III

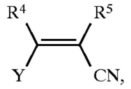

(III)

in which $R^4$ and $R^5$ have the meanings given in general formula I and Y is $C_1$–$C_6$-alkoxy, hydroxy or halogen, or when $R^5$ is hydrogen, B) a compound of general formula II

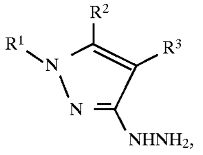

(II)

in which $R^1$, $R^2$ and $R^3$ have the meanings given in general formula I, is reacted with a 2-haloacrylonitrile of formula IIIa

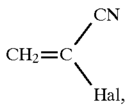

(IIIa)

or with a 2,3-dihalopropionitrile of formula IIIb

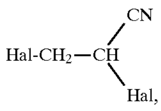

(IIIb)

in which Hal is halogen, or when $R^3$ is halogen,

C) a compound of general formula Ia

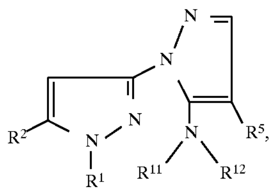

(Ia)

in which $R^1$, $R^2$, $R^5$, $R^{11}$ and $R^{12}$ have the meanings given in general formula I, is reacted first with a halogenating agent to give a compound of formula Ib

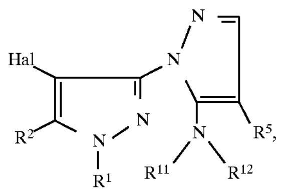

(Ib)

in which $R^1$, $R^2$, $R^5$, $R^{11}$ and $R^{12}$ have the meanings given in general formula I, and Hal is halogen, and then further treated to give the desired compound, or when $R^5$ is —C(=S)$R^{10}$ and $R^6$ is amino, D) a compound of general formula Ic

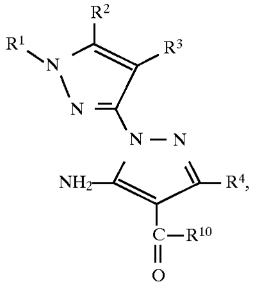

(Ic)

in which $R^1$, $R^2$, $R^3$, $R^4$ and $R^{10}$ have the meanings given in general formula I, is treated with Lawesson's reagent, or when $R^3$ is —$OR^{16}$, E) a compound of general formula Id

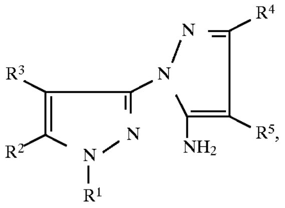

(Id)

in which $R^1$, $R^2$, $R^3$, $R^4$ and $R^5$ have the meanings given in general formula I, is first diazotised to give a compound of formula Ie

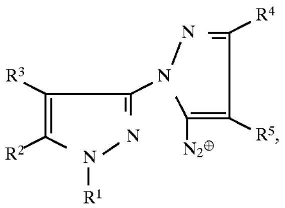

(Ie)

in which $R^1$, $R^2$, $R^3$, $R^4$ and $R^5$ have the meanings given in general formula I, and then by heating to give a compound of formula If

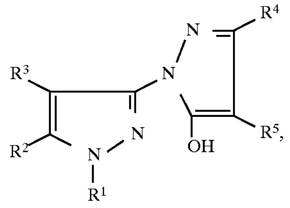

(If)

in which $R^1$, $R^2$, $R^3$, $R^4$ and $R^5$ have the meanings given in general formula I, which is then reacted with a compound of general formula IV $QR^{16}$ (IV)

in which $R^{16}$ has the meaning given in general formula I, and Q is a leaving group, or when $R^5$ is nitro and $R^6$ is —$SR^{17}$, F) a compound of general formula Ig (Ig)

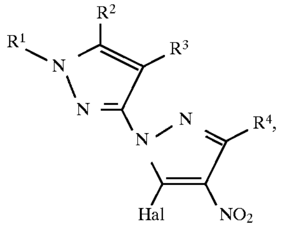

in which $R^1$, $R^2$, $R^3$ and $R^4$ have the meanings given in general formula I and Hal is halogen is reacted with a nucleophile of general formula V $^{\ominus}SR^{17}$ (V)

in which $R^{17}$ has the meaning given in general formula I, or when $R^5$ is nitro and $R^6$ is —$S(O)_nR^{17}$, in which n is 1 or 2, G) a compound of general formula Ih (Ih)

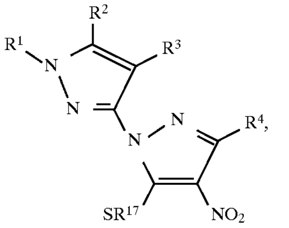

in which $R^1$, $R^2$, $R^3$, $R^4$ and $R^{17}$ have the meanings given in general formula I, is subjected to a stepwise oxidation with m-chloroperbenzoic acid, or when $R^5$ is cyano H) a compound of general formula IIa (IIa)

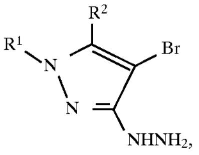

in which $R^1$ and $R^2$ have the meanings given in general formula I, is reacted with a compound of general formula IIIc (IIIc)

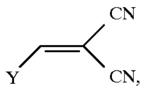

in which Y is $C_1$–$C_6$-alkoxy, hydroxy or halogen, or when $R^5$ is nitro,

I) a compound of general formula Ii (Ii)

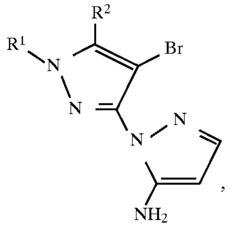

in which $R^1$ and $R^2$ have the meanings given in general formula I, is nitrated in known manner, or J) a compound of general formula Ij (Ij)

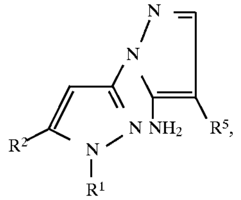

in which $R^1$, $R^2$ and $R^5$ have the meanings given in general formula I, is brominated in known manner, or when when $R^5$ is halogen, K) a compound of general formula II (II)

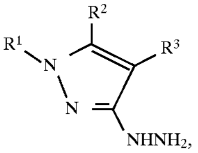

in which $R^1$, $R^2$ and $R^3$ have the meanings given in general formula I, is reacted with a compound of general formula IIIc (IIIc)

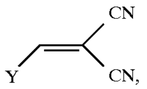

in which Y' is $C_1$–$C_6$-alkoxy, dimethylamino or halogen, to first give compound of formula Il (Il)

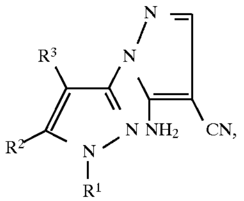

in which $R^1$, $R^2$ and $R^3$ have the meanings given in general formula I, and this compound is then diazotised in known manner with sodium nitrite and converted to the corresponding halide, or L) a compound of general formula Ik

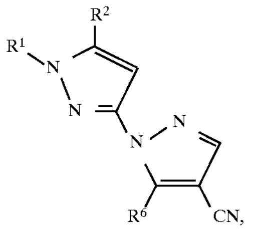

(Ik)

in which $R^1$, $R^2$ and $R^6$ have the meanings given in general is formula I, is treated with a halogenating agent, or M) a compound of general formula Im

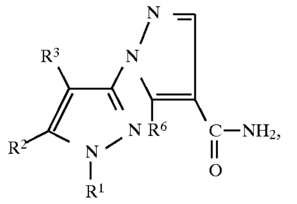

(Im)

in which $R^1$, $R^2$ and $R^3$ have the meanings given in general formula I, and $R^6$ is $C_1$–$C_4$-alkyl, (optionally substituted by one or more halogens) or is a $C_2$–$C_8$-alkyl, interrupted by one or more oxygens, is converted in known manner to the nitrile of general formula I, or when $R^6$ is —$NR^{11}R^{12}$, N) a compound of general formula In

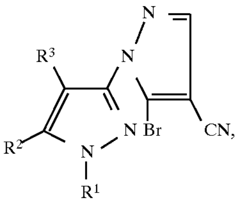

(In)

in which $R^1$, $R^2$ and $R^3$ have the meanings given in general formula I, is reacted with an amine in a solvent, or when $R^6$ is —$NR^{11}R^{12}$, in which $R^{11}$ is hydrogen and $R^{12}$ is $C_1$–$C_6$-alkyl, O) a compound of general formula Il

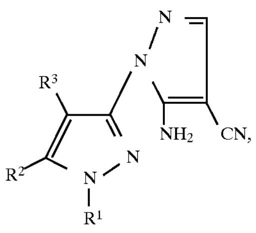

(Il)

in which $R^1$, $R^2$ and $R^3$ have the meanings given in general formula I, is reacted with a trialkyl ortho ester and then reduced, or P) a compound of general formula Io

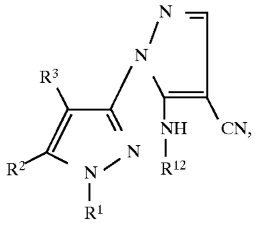

(Io)

in which $R^1$, $R^2$ and $R^3$ have the meanings given in general formula I, and $R^{12}$ is $C_1$–$C_6$-alkyl is reacted with an base and an alkylating agent or an acid chloride, or when $R^6$ is —$NR^{11}R^{12}$, in which $R^{11}$ and $R^{12}$ are $C_1$–$C_6$-alkyl, Q) a compound of general formula Il

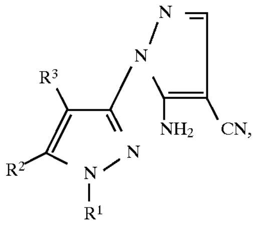

(Il)

in which $R^1$, $R^2$ and $R^3$ have the meanings given in general formula I, is reacted with approximately 2 mole of base and 2 mole of a suitable alkylating agent, or R) a compound of general formula Il

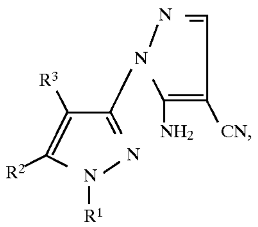

(Il)

in which $R^1$, $R^2$ and $R^3$ have the meanings given in general formula I, is reacted with or without a base and a suitable acid chloride, or S) a compound of general formula Ip

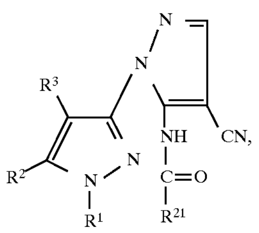

(Ip)

in which $R^1$, $R^2$, $R^3$ and $R^{21}$ have the meanings given in general formula I, is reacted with a base and a suitable alkylating agent, or T) a compound of general formula In

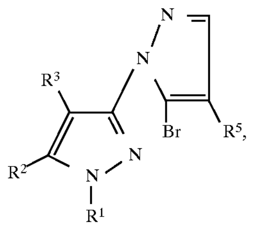

(In)

in which $R^1$, $R^2$ and $R^3$ have the meanings given in general formula I and $R^5$ is cyano or nitro, is reacted with an oxygen, nitrogen, sulfur or carbon nucleophile, or when $R^6$ is substituted methyl U) a compound of general formula Iq

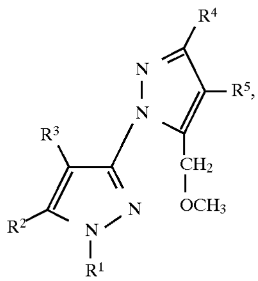

(Iq)

in which $R^1$, $R^2$, $R^3$, $R^4$ and $R^5$ have the meanings given in general formula I, is reacted with a Lewis acid, or V) a compound of general formula Ir

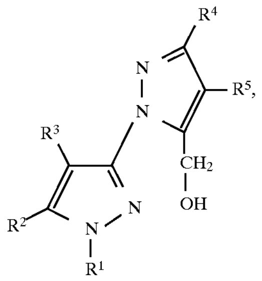

(Ir)

in which $R^1$, $R^2$, $R^3$, $R^4$ and $R^5$ have the meanings given in general formula I, is treated with a halogenating agent, or W) a compound of general formula Is

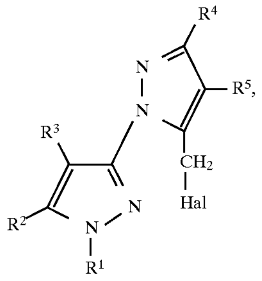

(Is)

in which $R^1$, $R^2$, $R^3$, $R^4$ and $R^5$ have the meanings given in general formula I, is reacted with an oxygen, nitrogen, sulfur or carbon nucleophile, or when $R^6$ is mercapto X) a compound of general formula It

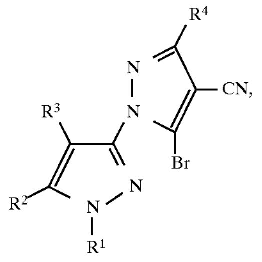

(It)

in which $R^1$, $R^2$, $R^3$ and $R^4$ have the meanings given in general formula I, is treated with sodium hydrogen sulfide, or Y) a compound of general formula Iu

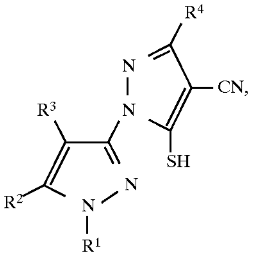

(Iu)

in which $R^1$, $R^2$, $R^3$ and $R^4$ have the meanings given in general formula I, is treated with a suitable alkylating agent, or Z) a compound of general formula Iv

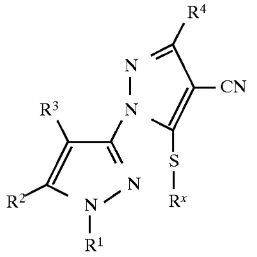

(Iv)

in which $R^1$, $R^2$, $R^3$ and $R^4$ have the meanings given in general formula I, and $R^x$ is $C_1$–$C_4$-alkyl, is oxidised in stages.

The compounds of the invention of general formula I, in which $R^5$ is nitro and $R^6$ is halogen, can also be prepared according to the process described in DE 3501323.

The compounds of the invention of general formula I, in which $R^5$ is the group —C(O)$R^{10}$ and $R^6$ is amino, can also be prepared according to the process described in Collect. Czech. Chem. Commun. 55, 1038–48 (1990).

The compounds of the invention of general formula I, in which $R^6$ is the group —$NR^{11}R^{12}$, can also be prepared according to the known processes described in DE 3 707 686, DE 3 543 034, EP 224 831, DE 3 543 035, JP 57167972 and DE 2 747 531.

The compounds of the invention of general formula I, in which $R^{14}$ is the group —$OR^{18}$ or —$NR^{19}R^{20}$, can be prepared from compounds of general formula I, in which $R^6$ is amino according to the known processes described in Chem. Soc. Rev. 4, 231–50 (1975) and J. March, Advanced Organic Chemistry, 1985, p. 370.

The compounds of the invention of general formula I, in which $R^5$ is cyano or nitro and $R^6$ is $C_1$–$C_4$-alkyl, can be prepared according to known processes (J. Heterocyclic Chem. 24, 1669 (1987), ibid. 24, 739 (1987).

The reactions are suitably carried out by reacting the compounds of formulae II, IIa or III in a suitable solvent at a temperature between −30° and 150° C., preferably at room temperature.

As halogenating agent there can be used for example sulfuryl chloride, sodium hypochlorite, N-chlorosuccinimide, N-bromosuccinimide, bromine or chlorine.

Leaving groups in process variant E are chloro or bromo.

The nitration in process variant I) is suitably carried out in known manner with nitric acid in acetic anhydride. The reaction temperature lies in the region of −10° to 140° C.

The process variant J) is suitably carried out in a solvent at a temperature of −20° C. up to the boiling point of the solvent.

As brominating agent in process variant J) there can be used, for example N-bromosuccinimide or bromine.

The reaction of compounds of general formula Il is suitably carried by the method described in J. March, Advanced Organic Chemistry, 1985, p. 647.

The process variant L) is generally carried out in a suitable solvent, preferably acetonitrile or dichloromethane, at a temperature of between −10° C. and 80° C.

Process variant M) is generally carried out according to the method described in Tetrahedron Letters, 1977 p. 1813.

Process variant O) is generally carried out according to the known methods (J. March, Advanced Organic Chemistry, 1985, p. 798–800 and literature cited there).

Suitable bases for process variants P), Q), R) and S) include for example alkali metal and alkaline earth metal hydroxides, sodium methanolate, alkali metal hydrides, alkali metal and alkaline earth metal carbonates, tertiary aliphatic and aromatic amines, such as triethylamine and pyridine as well as heterocyclic bases.

Process variant T) is generally carried out for example according to methods described in J. Heterocyclic Chem. 25, 555 (1988).

The preparation can be carried out with or without a solvent. Should need arise, such solvent or diluents can be used which are inert to the reactants. Examples of such solvents or diluents are aliphatic, alicyclic and aromatic hydrocarbons, each of which can be optionally chlorinated, such as for example hexane, cyclohexane, petroleum ether, naphtha, benzene, toluene, xylene, methylene chloride, chloroform, carbon tetrachloride, ethylene dichloride, trichloroethane and chlorobenzene, ethers, such as for example diethyl ether, methyl ethyl ether, methyl t-butyl ether, diisopropyl ether, dibutyl ether, dioxane and tetrahydrofuran, ketones, such as for example acetone, methyl ethyl ketone, methyl isopropyl ketone and methyl isobutyl ketone, nitriles, such as for example acetonitrile and propionitrile, alcohols, such as for example methanol, ethanol, isopropanol, butanol, tert-butanol, tert-amyl alcohol and ethylene glycol, esters, such as for example ethyl acetate and amyl acetate, amides, such as for example dimethylformamide and dimethylacetamide, sulfoxides, such as for example dimethyl sulfoxide and sulfones such as for example sulfolane, bases, such as for example pyridine and triethylamine, carboxylic acids such as for example acetic acid, and mineral acids such as for example sulfuric acid and hydrochloric acid.

The compounds of the invention can be worked up in conventional manner. Purification can be achieved by crystallisation or column chromatography.

The compounds of the invention are, as a rule, colourless or slightly yellow crystalline or liquids or substances that are highly soluble in halogenated hydrocarbons, such as methylene chloride or chloroform, ethers, such as diethyl ether or tetrahydrofuran, alcohols, such as methanol or ethanol, ketones, such as acetone or butanone, amides, such as dimethylformamide, and also sulfoxides, such as dimethyl sulfoxide.

The intermediate compounds of general formula II

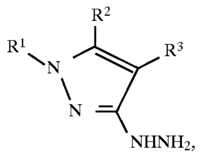

(II)

in which $R^1$, $R^2$ and $R^3$ have the meanings given in general formula I can be prepared in known manner (e.g. JP 62158260) from compounds of general formula VI

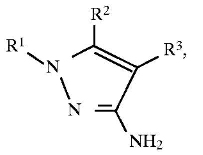

(VI)

in which $R^1$, $R^2$ and $R^3$ have the meanings given in general formula I.

The compounds of general formula II in which $R^1$ and $R^2$ together form the group $—(CH_2)_m—$ and $R^3$ is hydrogen, can be prepared by treating a compound of general formula IIIc

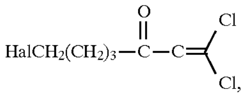

(IIIc)

with hydrazine with addition of a base. The compound of general formula IIIc can be prepared by reacting a compound of general formula IIId

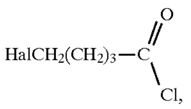

(IIId)

and a 1,1-dihaloethylene.

The compounds of general formula VI, in which $R^1$ and $R^2$ have the meanings given in general formula I and $R^3$ is halogen, can be prepared by reacting a compound of general formula VI in which $R^3$ is hydrogen, with a halogenating agent.

The compounds used as starting materials for compounds of general formula VI, are of general formula VII

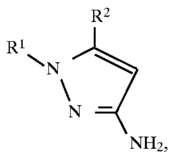

(VII)

in which $R^1$ has the meaning given in general formula I, and can be prepared for example, by a process in which, in the case when $R^2$ is $C_1$–$C_4$-alkyl, optionally substituted by halogen, a) a compound of general formula VIII, VIIIa or IX

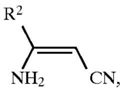

(VIII)

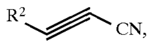

(VIIIa)

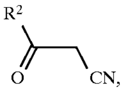

(IX)

in which $R^2$ is $C_1$–$C_4$-alkyl, optionally substituted by halogen, is reacted with a compound of general formula X $R^1$—NHNH2 (X)

in which $R^1$ has the meaning given in general formula I, optionally in the presence of a solvent, or when $R^2$ is $C_1$–$C_4$-alkylthio, optionally substituted by one or more halogens, b) a compound of general formula XI

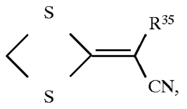

(XI)

in which $R^{35}$ is cyano or the group —$COOR^{36}$, in which $R^{36}$ is $C_1$–$C_4$-alkyl, is reacted with a compound of general formula X, optionally in the presence of a solvent, e.g. water, to give first a compound of general formula XII

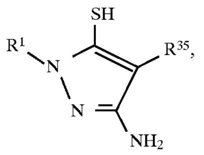

(XII)

in which $R^1$ has the meaning given in general formula I and $R^{35}$ has the meaning given above, which is then reacted with a compound of general formula XIII $R^{37}Q$ (XIII)

in which $R^{37}$ is $C_1$–$C_4$-alkyl, optionally substituted by one or more halogens, and Q is a leaving group, and the resulting compound of general formula XIV

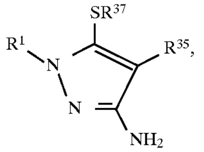

(XIV)

is saponified and decarbcxylated according to known literature methods (e.g. Zeitschrift für Chemie 420, (1968)), or c) a compound of general formula XV

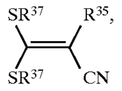

(XV)

in which $R^{35}$ is cyano or the group —$COOR^{36}$, in which $R^{36}$ is $C_1$–$C_4$-alkyl, and $R^{37}$ is $C_1$–$C_4$-alkyl, optionally substituted by one or more halogens, is reacted with a compound of general formula X, optionally in the presence of a solvent, e.g. water, to give a compound of general formula XIV, or when $R^2$ is $C_1$–$C_4$-alkoxy, optionally substituted by one or more halogens d) a compound of general formula XVI

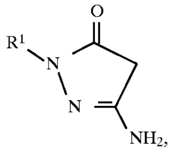

(XVI)

in which $R^1$ has the meaning given in general formula I, is reacted with a compound of general formula XIII, in the presence of a base, or h) a compound of general formula XVII

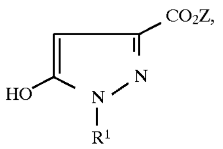

(XVII)

in which $R^1$ has the meaning given in general formula I and Z is $C_1$–$C_4$-alkyl, is reacted, in the presence of a base, with a compound of general formula XIII $R^{37}Q$ (XIII)

in which $R^{37}$ is $C_1$–$C_4$-alkyl, optionally substituted by one or more halogens, and Q is a leaving group, and the resulting compound of general formula XVIII

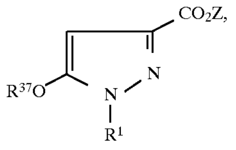

(XVIII)

in which $R^1$ has the meaning given in general formula I, $R^{37}$ is $C_1$–$C_4$-alkyl, optionally substituted by one or more halogens, and Z is $C_1$–$C_4$-alkyl, is reacted with ammonia and the resulting compound of general formula XIX

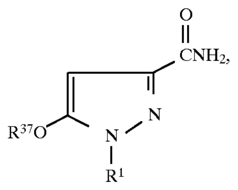

(XIX)

in which $R^1$ as the meaning given in general formula I and $R^{37}$ is $C_1$–$C_4$-alkyl, optionally substituted by one or more halogens, is reacted with sodium hydroxide and a halogen, or when $R^3$ in general formula I is halogen, f) a compound of general formula XVIII or XIX

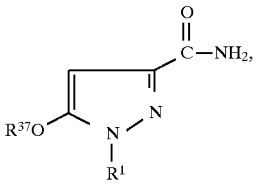
(XIX)

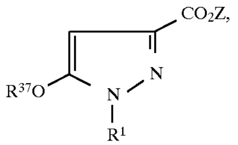
(XIII)

in which $R^1$ has the meaning given in general formula I, $R^{37}$ is $C^1$–$C_4$-alkyl, optionally substituted by one or more halogens, and Z is $C^1$–$C_4$-alkyl, is reacted with a halogenating agent to give a compound of general formula XVIIIa and XIXb

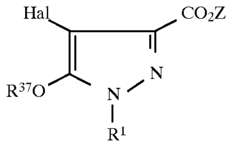
(XVIIIa)

und

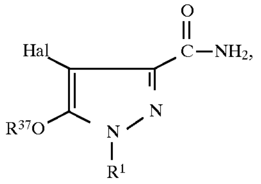
(XIXb)

in which $R^1$, $R^{37}$ and Z have the meanings given in general formula XVIII and XIX, or g) a compound of general formula XIXa

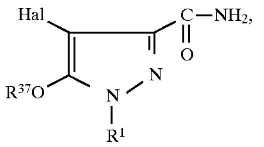
(XIXa)

in which $R^1$ has the meaning given in general formula I, $R^{37}$ is $C_1$–$C_4$-alkyl, optionally substituted by one or more halogens, and Hal is halogen, is reacted with sodium hydroxide and bromine to give a compound of general formula XX

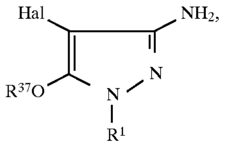
(XX)

in which $R^1$, $R^{37}$ and Hal have the meanings given in formula XIXa, or when $R^1$ and $R^2$ together form a tri- or tetramethylene group h) a compound of general formula XXI

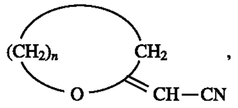
(XXI)

in which n is 2 or 3, is reacted with hydrazine and the resulting 3(5)-amino-5(3)-hydroxyalkylpyrazole of general formula XXII

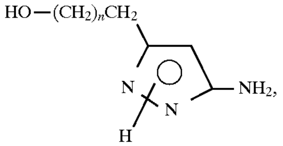
(XXII)

in which n is 2 or 3, is reacted with hexane-2,5-dione, phthalic anhydride or tetrahydrophthalic anhydride, in a similar manner to known literature methods (Bull. Chem. Soc. Jp., 44, 2856–8 (1971), or EP 305826), to give a compound of general formula XXIII

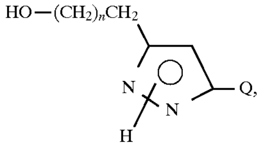
(XXIII)

in which n is 2 or 3 and Q is an amino protecting group, such as e.g. $Q_1$, $Q_2$ or $Q_3$

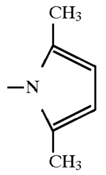
($Q_1$)

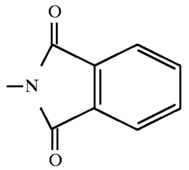
($Q_2$)

oder

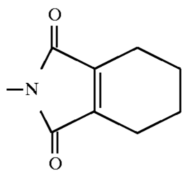
($Q_3$)

and this is cyclised using the Mitsunobu variant (Synthesis, 1 (1981)), to give a compound of general formula XXIV

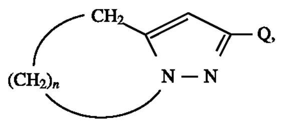
(XXIV)

in which n is 2 or 3, and then in the case when Q is $Q_1$, this is treated with hydroxylamine as described in J. Org. Chem., 49, 1224–1227 (1984), and in the case when Q is $Q_2$ or $Q_3$, this is treated with hydrazine, in a similar manner to known literature methods (Org. Synthesis, Coll. Vol., 3, 148 (1955)).

The starting materials of general formula XXI can be prepared in known manner (Chem. Ber., 109(1), 253–60, 1976).

The compounds of general formula Ii, used as starting materials, can be prepared by decarboxylating a compound of general formula XXV

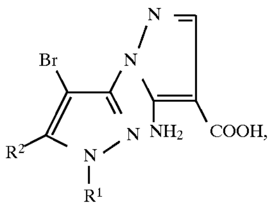

(XXV)

in which $R^1$ and $R^2$ have the meanings given in general formula I.

The compounds of general formula XXV can be prepared by saponifying a compound of general formula XXVI

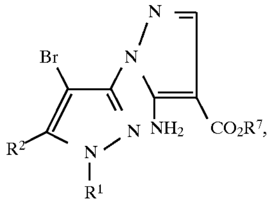

(XXVI)

in which $R^1$ and $R^2$, have the meanings given under general formula I and $R^7$ is $C_1$–$C_4$-alkyl.

The compounds of general formula XXVI can be prepared by reacting a compound of general IIa, in which $R^1$ and $R^2$ have the meanings given under general formula I with a compound of general formula XXVII

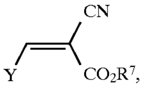

(XXVII)

in which $R^7$ is $C_1$–$C_4$-alkyl and Y is $C_1$–$C_6$-alkoxy, hydroxy or halogen.

The intermediates of general formula Ij, can be prepared in an analogous way to process described above in which instead of the compounds of general formulae IIa and Ii the corresponding compounds of general formula XXVIII and/or XXIX

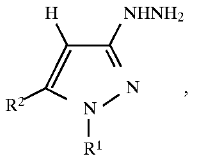

(XXVIII)

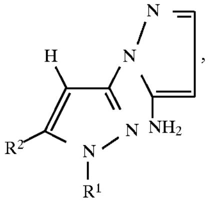

(XXIX)

are used.

The intermediates of general formula Ik, can he prepared by reacting a compound of general formula IIb

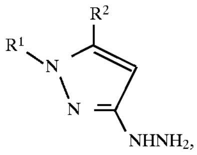

(IIb)

in which $R^1$ and $R^2$ have the meanings given in general formula IIb in an analogous way to processes described above.

The intermediates of general formula Im, in which $R^6$ is $C_1$–$C_4$-alkyl, optionally substituted by one or more halogens or $C_2$–$C_8$-alkyl, interrupted by one or more oxygen atoms, can be prepared converting a compound of general formula Iq

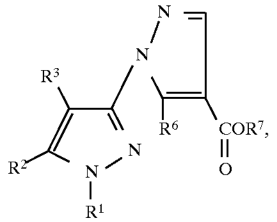

(Iq)

in which $R^1$, $R^2$ and $R^3$ have the meanings given in general formula I, $R^6$ is $C_1$–$C_4$-alkyl, optionally substituted by one or more halogens or $C_2$–$C_8$-alkyl, interrupted by one or more oxygen atoms, and $R^7$ is $C_1$–$C_4$-alkyl, in known manner to the amide.

The compounds of general formula Iq can be prepared in known manner (J. Heterocyclic Chem 24, 1669 (1987), ibid. 24, 739 (1987)).

The preparation of the intermediates can be carried out with or without a solvent. Should need arise, a solvent mentioned above can be used.

The named starting materials are either known in the or can be prepared in similar manner to known methods.

The compounds of the invention show a good herbicidal activity against broad leaved weeds and grasses. A selective use of the compounds of the invention in various crops is possible for example in rape, beet, soya beans, cotton, rice, barley, wheat and other cereals. Individual active substances are particularly suitable as selective herbicides in beet, cotton, soya, maize and cereals. However the compounds can be used for control of weeds in permanent crops, such as for example forestry, ornamental trees, fruit, vine, citrus, nut, banana, coffee, tea, rubber, oil palm, cocoa, berry fruit and hop plantations.

The compounds of the invention can used for example against the following plant species:

Dicotyledonous weeds of the species: Sinapis, Lepidium, Galium, Stellaria, Matricaria, Anthemis, Galinsoga, Chenopodium, Brassica, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Lamium, Veronica, Abutilon, Datura, Viola, Galeopsis, Papaver, Centaurea and Chrysanthemum.

Monocotyledonous weeds of the species: Avena, Alopecurus, Echinochloa, Setaria, Panicum, Digitaria, Poa, Eleusine, Brachiaria, Lolium, Bromus, Cyperus, Agropyron, Sagittaria, Monocharia, Fimbristylis, Eleocharis, Ischaemum and Apera.

The rates of use vary depending on the manner of pre- and postemergent use between 0.001 and 5 kg/ha.

The compounds of the invention can also be used as defoliants, desiccants and total herbicides.

The compounds of the invention can be used either alone or in admixture with one another or with other active agents.

Optionally, other plant-protective agents or pesticides can be added, depending on the purpose for the treatment. When it is desired to broaden the spectrum of activity, other herbicides can also be added. Herbicidally active mixing partners suitable in this connection include for example, the active agents listed in Weed Abstracts, vol. 40, No. 1, 1991, under the heading "Lists of common names and abbreviations employed for currently used herbicides and plant growth regulators in Weed Abstracts".

An improvement in the intensity and speed of action can be obtained, for example, by addition of suitable adjuvants, such as organic solvents, wetting agents and oils. Such additives may allow a decrease in the dose.

The designated active ingredients or their mixtures can suitably be used, for example, as powders, dusts, granules, solutions, emulsions or suspensions, with the addition of liquid and/or solid carriers and/or diluents and, optionally, binding, wetting, emulsifying and,/or dispersing adjuvants.

Suitable liquid carriers are, for example aliphatic and aromatic hydrocarbons, such as benzene, toluene, xylene, cyclohexanone, isophorone, dimethyl sulfoxide, dimethylformamide and other mineral-oil fractions and plant oils.

Suitable solid carriers include mineral earths, e.g. bentonite, silica gel, talcum, kaolin, attapulgite, limestone, silicic acid and plant products, e.g. flours.

As surface-active agents there can be used for example calcium lignosulfonate, polyoxyethylenealkylphenyl ethers, naphthalenesulfonic acids and their salts, phenolsulfonic acids and their salts, formaldehyde condensates, fatty alcohol sulfates, as well as substituted benzenesulfonic acids and their salts.

The percentage of the active ingredient(s) in the various preparations can vary within wide limits. For example, the compositions can contain about 10 to 90 percent by weight active ingredients, and about 90 to 10 percent by weight liquid or solid carriers, as well as, optionally up to 20 percent by weight of surfactant.

The agents can be applied in customary fashion, for example with water as the carrier in spray mixture volumes of approximately 100 to 1,000 l/ha. The agents can be applied using low-volume or ultra-low-volume techniques or in the form of so-called microgranules.

The preparation of these formulations can be carried out in known manner, for example by milling or mixing processes. Optionally, individual components can be mixed just before use for example by the so-called commonly used tank-mixing method.

Formulations can be prepared, for example, from the following ingredients.

A) Wettable Powder

- 20 percent by weight active ingredient
- 35 percent by weight fuller's earth
- 8 percent by weight calcium lignosulfonate
- 2 percent by weight sodium salt of N-methyl-N-oleyltaurine
- 25 percent by weight silicic acid B) Paste

- 45 percent by weight active ingredient
- 5 percent by weight sodium aluminium silicate
- 15 percent by weight cetyl polyglycol ether with 8 mole ethylene oxide
- 2 percent by weight spindle oil
- 10 percent by weight polyethylene glycol
- 23 percent by weight water C) Emulsifiable Concentrate

- 20 percent by weight active ingredient
- 75 percent by weight isophorone
- 5 percent by weight of a mixture of the sodium salt of N-methyl-N-oleyltaurine and calcium lignosulfonate The following examples illustrate the preparation of compounds according to the invention.

EXAMPLE 1.0

4-Acetyl-5-amino-1-(3-chloro-4,5,6,7-tetrahydromyrazolo-[1,5-a]pyridin-2-yl)pyrarole 0.56 g (3 mmol) 3-Chloro-2-hydrazino-4,5,6,7-tetrahydro-pyrazolo[1,5-a]pyridine was dissolved in 5 ml ethanol and treated with 0.42 g (3 mmol) 2-ethoxymethylen-3-oxobutyro-nitrile. After heating under reflux for 3 hours, the mixture was concentrated and the residue purified by silica gel chromatography (hexane/ethyl acetate 1:1).

Yield: 0.75 g=89.4% of theory; mp: 153°–154° C.

EXAMPLE 1.1

5-Amino-1-(3-chloro-4,5,6,7-tetrahydropyrazolo-[1,5-a]pyridin-2-yl)-4-thioacetylpyrazole 0.28 g (1 mmol) 4-Acetyl-5-amino-1-(3-chloro-4,5,6,7-tetrahydropyrazolo[1,5-a]pyridin-2-yl)pyrazole was dissolved in 5 ml dimethoxyethane and treated with 0.28 (0.6 mmol) Lawesson's reagent. After heating under reflux for 2 hours with stirring, the reaction solution was poured into water and extracted with ethyl acetate. The organic phase was washed with saturated aqueous sodium chloride, dried over magnesium sulfate and concentrated. The residue was purified by silica gel column chromatography. (Hexane/ethyl acetate 1:1).

Yield: 0.21 g=71% of theory; mp: 166°–167° C.

EXAMPLE 1.2

N-[1-(3-Chloro-4,5,6,7-tetrahydropyrazolo[1,5-a]pyridin-2-yl) -4-nitro-5-pyrazolyl]propionamide 8.72 g (29.7 mmol) N-[1-(3-Chloro-4,5,6,7-tetrahydropyrazolo[1,5-a]pyridin-2-yl)-5-pyrazolyl]propionamide was suspended in 33 ml acetic acid. Under ice cooling, at 0°–5° C., 3.31 g (32.5 mmol) acetic anhydride was added. 1.93 g (31 mmol) Fuming nitric acid was added dropwise. After stirring for 6 hours at room temperature, the mixture was concentrated. The residue was taken up in dichloromethane, neutralised with aqueous sodium hydrogen carbonate and washed with aqueous sodium chloride. The organic phase was dried over magnesium sulfate and concentrated. The residue was purified by silica gel chromatography (hexane/ethyl acetate 1:1).

Yield: 6.03 g=60% of theory; mp: 46°–49° C.

EXAMPLE 2.0

N-[1-(4-Chloro-5-difluoromethoxy-1-methyl-3-pyrazolyl)-4-nitro-5-pyrazolyl]-2,2,2-trifluoroacetamide 0.79 g (2.1 mmol) N-[1-(5-Difluoromethoxy-1-methyl-3-pyrazolyl)-4-nitro-5-pyrazolyl]-2-2,2-trifluoroacetamide was suspended in 35 ml dichloromethane and treated with 0.17 ml sulfuryl chloride. The mixture was stirred for one hour at room temperature and concentrated.

Yield: 0.77 g=89.5% of theory; mp: 136°–139° C.

EXAMPLE 2.1

N-[1-(4-Chloro-5-difluoromethoxy-1-methyl-3-pyrarolyl) -4-nitro-5-pyrarolyl]acetamide 1.3 g (5.0 mmol) 5-Amino-1-(4-chloro-5-difluoromethoxy-1-methyl-3-pyrazolyl)pyrazole was dissolved in 20 ml acetic acid and treated with 0.55 g (5.4 mmol) acetic anhydride. After stirring for 2 hours at room temperature the reaction solution was cooled to 0° C. and 0.4 g (6.4 mmol) concentrated nitric acid added. After stirring for 8 hours at room temperature, the reaction mixture was poured into ice water and extracted with ethyl acetate. The organic phase was dried over magnesium sulfate and concentrated. The residue was purified by silica gel column chromatography (hexane/ethyl acetate 1:1).

Yield: 1.4 g=81.5% of theory; mp: 132° C.

EXAMPLE 3.1

5-Amino-4-nitro-1-(4-bromo-5-difluoromethoxy-1-methyl-3-pyrazolyl)pyrazole 8.3 g (0.052 mol) Bromine was added dropwise at room temperature to 13 g (0.047 mol) 5-amino-4-nitro-1-(5-difluoromethoxy-1-methyl-3-pyrazolyl)pyrazole dissolved in 260 ml acetic acid and the mixture stirred for 30 minutes. It was then concentrated and the residue taken up in the ethyl acetate and shaken with 5% aqueous sodium hydrogen carbonate. The phases were separated and the organic phase dried over magnesium sulfate. This was concentrated and the residue purified by silica gel column chromatography (hexane/ethyl acetate 3:1).

Yield: 8.3 g=49.6% of theory; mp: 148° C.

Preparation of the starting materials 1. 5-Amino-4-nitro-1-(5-difluoromethoxy-1-methyl-3-pyrazolyl)-pyrazole 15 g (0.065 mol) 5-Amino-1-(5-difluoromethoxy-1-methyl-3-pyrazolyl)pyrazole was dissolved in 60 ml acetic acid and treated with 7.35 g (0.072 mol) acetic anhydride. After stirring at room temperature for 3 hours, the reaction mixture was cooled to 10° C. 4.95 g (0.078 mol) Fuming nitric acid was added dropwise and the mixture treated with 8.0 g (0.078 mol) acetic anhydride. After stirring for 18 hours at room temperature, the reaction mixture was added to 500 ml ice-water. It was extracted three times with ethyl acetate, the organic phases were washed with water and concentrated. The residue was treated with 80 ml ethanol and 40 ml concentrated hydrochloric acid. After heating for 8 hours under reflux, the ethanol was removed and the residue extracted with ethyl acetate. The concentrated ethyl acetate phases were washed with saturated aqueous sodium hydrogen carbonate, dried over magnesium sulfate and concentrated. The residue was recrystallised from diisopropyl ether and ethyl acetate.

Yield: 10 g=56% of theory; mp: 140° C.

2. 5-Amino-1-(5-difluoromethoxy-1-methyl-3-pyrazolyl)-pyrazole 16.5 (0.06 mol) 5-Amino-1-(5-difluoromethoxy-1-methyl-3-pyrazolyl)-4-pyrazolecarboxylic acid was heated at 210° C. for 5 minutes and then cooled. The congealed melt was recrystallised from diisopropyl ether.

Yield: 12.6 g=92% of theory; mp: 106°–107° C.

3. 5-Amino-1-(5-difluoromethoxy-1-methyl-3-pyrazolyl)-4-pyrazolecarboxylic acid 18.9 g (0.06 mol) Ethyl 5-Amino-1-(5-difluoromethoxy-1-methyl-3-pyrazolyl)-4-pyrazolyl-4-pyrazolecarboxylate was dissolved in 150 ml 50% ethanol and treated with 15 ml 45% caustic soda. The mixture was heated for 2 hours at 80° C., the ethanol distilled, the residue treated with ice-water and acidified with concentrated hydrochloric acid. The residue was removed by suction filtration, washed with water and dried in vacuo at 75° C.

Yield: 16.7 g=97% of theory; mp: 173° C. (dec.)

4. Ethyl 5-Amino-1-(5-difluoromethoxy-1-methyl-3-pyrazolyl)-4-pyrazolyl-4-pyrazolecarboxylate 19 g (0.1 mol) 5-Difluoromethoxy-3-hydrazino-1-methyl-pyrazole was dissolved in 100 ml ethanol. 18.05 g (0.1 mol) Ethyl ethoxymethylenecyanoacetate was added and the mixture heated for 1.5 hours at boiling. After cooling, the precipitated product was removed by suction filtration, washed with some ethanol and dried.

Yield: 18.95 g=59% of theory; mp: 168°–169° C.

5. 5-Difluoromethoxy-3-hydrazino-1-methylpyrazole 39.8 g (0.25 mol) 3-Amino-5-difluoromethoxy-1-methyl-pyrazole was dissolved in 224 ml water and 450 ml concentrated hydrochloric acid. At −10° C., 18.55 g (0.27 mol) sodium nitrite in 80 ml water was added dropwise. After stirring for 1 hour at −10° C., 137.6 g tin(II)chloride, dissolved in 180 ml concentrated hydrochloric acid, was added, dropwise, at this temperature. After a further hour stirring at −10° C., 805 ml 32% caustic soda was added dropwise at this temperature. The reaction mixture was shaken 8 times with ethyl acetate, the combined organic phases washed with saturated aqueous sodium chloride, dried over magnesium sulfate and concentrated.

Yield: 42.24 g=97.2% of theory

EXAMPLE 3.2

5-Amino-1-(4-bromo-5-difluoromethoxy-1-methyl-3-pyrazolyl)-4-pyrazolecarbonitrile 5.0 g (20 mmol) 5-Amino-1-(5-difluoromethoxy-1-methyl-3-pyrazolyl)-4-pyrazolecarbonitrile was dissolved in 80 ml acetic acid. At room temperature, 1.2 ml (23 mmol) bromine was added, dropwise. After stirring for 15 minutes, the mixture was concentrated and stirred with diisopropyl ether/propanol. The solid material was suction filtered and dried.

Yield: 5.7 g=87% of theory; mp: 160° C.

EXAMPLE 3.3

5-Amino-1-(3-bromo-4,5,6,7-tetrahydropyrazolo-[1,5-a]-pyridin-2-yl)-4-nitropyrazole 3.6 g (12.7 mmol) 5-Amino-1-(3-bromo-4,5,6,7-tetrahydropyrazolo[1,5-a]pyridin-2-yl)pyrazole was suspended in 15 ml acetic acid and treated with 1.23 ml (13.0 mmol) acetic anhydride. The mixture was stirred for 5 hours at room temperature. 1.5 ml (15.9 mmol) acetic anhydride was added and then, with ice-bath cooling, 0.66 ml (15.5 mmol) fuming nitric acid was added, dropwise. After stirring for 12 hours at room temperature, the mixture was concentrated. The residue was dissolved in 30 ml ethanol and treated with 11.2 ml concentrated hydrochloric acid. After heating for 3 hours under reflux, the mixture was concentrated and the residue taken up in water and ethyl acetate. It was made basic with 2N aqueous sodium hydroxide and the organic phase separated. The aqueous phase was extracted twice with ethyl acetate. The combined organic phases were washed once with water and once with saturated aqueous sodium chloride. The organic phase was dried and concentrated. The residue was recrystallised from ethyl acetate.

EXAMPLE 4.1

1-(3-Chloro-4,5,6,7-tetrahydropyrazolo[1,5-a]pyridin-2-yl)-5-diethylamino-4-pyrazolecarbonitrile 10.45 g (0.35 mol) Sodium hydride (80%) was added to 100 ml tetrahydrofuran and cooled to 0° C. In a nitrogen atmosphere, a suspension of 43.6 g (0.17 mol) 5-amino-1-(3-chloro-4,5,6,7-tetrahydropyrazolo-[1,5-a]pyridin-2-yl)-4-pyrazolecarbonitrile in 500 ml tetrahydrofuran was added dropwise. The mixture was stirred for 1.5 hours. Then 31.4 ml (0.38 mol) iodoethane in 20 ml tetrahydrofuran was added dropwise at 15° C. After stirring for three hours at 15° C., the mixture was cooled. Water was then added dropwise and the mixture extracted with ethyl acetate. The organic phase was separated, dried and concentrated. The residue was recrystallised from ethyl acetate.

Yield: 47.3 g=89.4% of theory; mp: 68°–70° C.

EXAMPLE 4.2

1-(3-Chloro-4,5,6 7-tetrahydropyrazolo[1,5-a]pyridin-2-yl)-5-(ethylmethylamino)-4-pyrazolecarbonitrile 23.3 g (88.7 mmol) 5-Amino-1-(3-chloro-4,5,6,7-tetrahydropyrazolo[1,5-a]pyridin-2-yl)-4-pyrazolecarbonitrile, 202 ml (1,21 mmol) triethyl orthoformate and 10 drops trifluoroacetic acid was heated for 5 hours with removal of water in a water bath at a temperature of 150° C. The reaction solution was concentrated, the residue was suspended in 250 ml ethanol and treated, portionwise, with cooling with 4.2 g (106.4 mmol) sodium borohydride. The mixture was heated to reflux until no more gas evolution was observed. Then the mixture was concentrated and the residue carefully added to ice-water. The mixture was extracted 3 times with methylene chloride and the extracts dried. The organic phase was concentrated. 2.61 g (87.1 mmol) Sodium hydride (80%) was added to 150 ml tetrahydrofuran and at 0° C., 24.1 g (87.1 mmol) of the resulting 1-(3-chloro-4,5,6,7-tetrahydropyrazolo-[1,5-a]pyridin-2-yl)-5-methylamino-4-pyrazolecarbonitrile in 500 ml tetrahydrofuran was added dropwise. After stirring for 1 hour at room temperature, 7.82 ml (95.8 mmol) iodoethane was added and the mixture heated at 70° C. for 3 hours. Water was added dropwise and the mixture extracted 3 times with ethyl acetate. The organic phase was separated, dried and concentrated. The residue was recrystallised from ethyl acetate.

Yield: 18.97 g=71% of theory; mp: 68°–69° C.

EXAMPLE 4.3

5-Bromo-1-(4-chloro-5-difluoromethoxy-1-methyl-3-pyrazolyl)-4-pyrazolecarbonitrile 5.68 g (19.7 mmol) 5-Amino-1-(4-chloro-5-difluoromethoxy-1-methyl-3-pyrazolyl)-4-pyrazolecarbonitrile was dissolved in 66.3 ml hydrobromic acid (47%) and the mixture cooled to −6° C. Under a nitrogen atmosphere, 2.36 g (34.2 mmol) sodium nitrite in 5.9 ml water was added dropwise. The mixture was stirred for 15 minutes at this temperature and heated to room temperature. 200 ml water was then added and the mixture extracted 4 times with methylene chloride. The organic phase was washed with saturated aqueous sodium hydrogen carbonate, dried over magnesium sulfate and concentrated.

Yield: 6.94 g=99.5% of theory; mp: 78° C.

Preparation of the starting materials 1. 5-Amino-1-(4-chloro-5-difluoromethoxy-1-methyl-3-pyrazolyl)-4-pyrazolecarbonitrile 5.0 g (19.7 mmol) 5-Amino-1-(5-difluoromethoxy-1-methyl-3-pyrazolyl)-4-pyrazolecarbonitrile was dissolved in 180 ml acetonitrile and 2.65 g (19.7 mmol) sulfuryl chloride added dropwise. The mixture was stirred for one hour at room temperature and concentrated.

Yield: 5.68 g=99.5% of theory; mp: 140°–142° C.

2. 5-Amino-1-(5-difluoromethoxy-1-methyl-3-pyrazolyl)-4-pyrazolecarbonitrile 22.5 g (0.13 mol) 5-Difluoromethoxy-3-hydrazino-1-methylpyrazole was dissolved in 310 ml ethanol and treated with 15.4 g (0.13 mol) ethoxymethylenemalononitrile. After the mixture had been heated under reflux for one hour it was cooled. The precipitate was suction filtered and washed with a small amount of ethanol.

Yield: 19.28 g=60% of theory; mp: 141°–143° C.

3. 5-Difluoromethoxy-3-hydrazino-1-methylpyrazole 39.8 g (0.25 mol) 3-Amino-5-difluorcmethoxy-1-methylpyrazole was dissolved in 225 ml water and 450 ml concentrated hydrochloric acid. At −10° C., 18.55 g (0.27 mol) sodium nitrite in 80 ml water was added dropwise. After stirring for one hour at −10° C., 137.6 g tin(II)chloride, dissolved in 180 ml concentrated hydrochloric acid, was added dropwise at this temperature. After stirring for a further hour at −10° C., 805 ml 32% caustic soda was added dropwise at this temperature to the reaction mixture. The mixture was shaken 8 times with ethyl acetate, the combined organic phases washed with aqueous saturated sodium chloride, dried over magnesium sulfate and concentrated.

Yield: 42.24 g=97.2% of theory 4. 3-Amino-5-difluoromethoxy-1-methylpyrazole 71.7 g (1.79 mol) Sodium hydroxide was added to 600 ml water and the mixture cooled to −5° C. At this temperature, 57.3 g (0.36 mol) bromine was added dropwise at such a rate that the temperature did not rise above 0° C. Then 57.1 g (0.3 mol) 3-carbamoyl-5-difluoromethoxy-1-methylpyrazole was added portionwise at 0° C. The reaction mixture was stirred for one hour at 80° C. and then saturated with sodium chloride. The precipitate which formed was suction filtered off. The filtrate was shaken 6 times with the ethyl acetate. The organic phase was dried over magnesium sulfate and concentrated. The precipitate which had been removed was dissolved in 500 ml water and the solution heated to boiling point for one hour. The reaction solution was saturated with sodium chloride and shaken 6 times with ethyl acetate. The organic phase was dried with magnesium sulfate and concentrated.

Yield: 34.2 g=70.5% of theory; mp: 57° C.

5. 3-Carbamoyl-5-difluoromethoxy-1-methylpyrazole 80.6 g (0.39 mol) 3-Methoxycarbonyl-5-difluoromethoxy-1-methylpyrazole and 300 ml aqueous ammonia (33%) was stirred for one hour under reflux. The reaction solution was cooled, the precipitate suction filtered off and washed with water and diisopropyl ether.

Yield: 58.9 g=78.8% of theory; mp: 154° C.

6. 5-Difluoromethoxy-3-methoxycarbonyl-1-methylpyrazole 67.6 g (0.43 mol) 5-Hydroxy-3-methoxycarbonyl-1-methylpyrazole and 299.2 g (2.17 mol) potassium carbonate was dissolved in 1500 ml dimethylformamide and heated to 70° C. At this temperature chlorodifluoromethane was introduced over 2 hours and the mixture stirred at 80° C. for 1.5 hours. The reaction mixture was added to water and extracted 6 times with ethyl acetate. The combined organic phases were washed with saturated aqueous sodium chloride and dried over magnesium sulfate. The reaction solution was concentrated.

Yield: 80.6 g=90.3% of theory 7. 5-Hydroxy-3-methoxycarbonyl-1-methylpyrazole 102.3 g (0.72 mol) Dimethyl acetylenedicarboxylate was added to 1000 ml ether and the mixture cooled to −5° C. in an ice-methanol bath. 33 g (0.72 mol) methylhydrazine in 100 ml ether was added dropwise at a rate that the inner temperature did not rise above 0° C. The mixture was stirred for one hour at 0° C., the precipitate suction filtered off, washed with ether and dried at 40° C. in vacuo. The intermediate was immersed in an oil-bath heated to 120° C. The reaction product was recrystallised from methanol.

Yield: 67.6 g=60.1% of theory; mp: 197° C.

8. 4-Chloro-5-difluoromethoxy-3-methoxycarbonyl-1-methyl-pyrazole 2.1 g (10 mmol) 5-Difluoromethoxy-3-methoxycarbonyl-1-methylpyrazole, dissolved in 30 ml methylene chloride, was treated with 1.35 g (10 mmol) sulfuryl chloride and the mixture stirred at room temperature for 10 minutes. It was then concentrated and the residue recrystallised from diisopropyl ether/ethyl acetate.

Yield: 1.8 g=74.8% of theory; mp: 51° C.

EXAMPLE 4.4

1-(4-Chloro-5-difluoromethoxy-1-methyl-3-pyrazolyl)-5-methyl-4-pyrazolecarbonitrile 0.57 g (2.25 mmol) 1-(5-Difluoromethoxy-1-methyl-3-pyrazolyl)-5-methyl-4-pyrazolecarbonitrile was dissolved in 30 ml methylene chloride and at room temperature was treated with 0.30 g (2.25 mmol) sulfuryl chloride. The mixture was stirred for one hour and then concentrated.

Yield: 0.65 g=99.8% of theory; mp: 69°–70° C.

Preparation of the starting materials 1. 1-(5-Difluoromethoxy-1-methyl-3-pyrazolyl)-5-methyl-4-pyrazolecarbonitrile A mixture of 0.79 g (2.91 mmol) 1-(5-difluoromethoxy-1-methyl-3-pyrazolyl)-5-methyl-4-pyrazolecarboxamide, 0.46 g (5.85 mmol) pyridine and 20 ml 1,4-dioxane was cooled to 5° C. and 0.74 g (3.51 mmol) trifluoroacetic anhydride was added dropwise. The mixture was stirred for 3 hours at room temperature. It was then added to 100 ml water and extracted 4 times with ethyl acetate. The organic phase was dried over magnesium sulfate and concentrated.

Yield: 0.74=99.8% of theory; mp: 106°–107° C.

2. 1-(5-Difluoromethoxy-1-methyl-3-pyrazolyl)-5-methyl-4-pyrazolecarboxamide 0.98 g (3.38 mmol) 1-(5-Difluoromethoxy-1-methyl-3-pyrazolyl)-5-methyl-4-pyrazolecarbonyl chloride was dissolved in 20 ml tetrahydrofuran and 50 ml aqueous ammonia (33%) was added with stirring. After stirring for 3 hours at room temperature, the mixture was concentrated to half and acidified with dilute hydrochloric acid. The precipitate was suction filtered off, washed with a small amount of water and dried.

Yield: 0.27 g=73% of theory; mp: 116°–118° C.

3. 1-(5-Difluoromethoxy-1-methyl-3-pyrazolyl)-5-methyl-4-pyrazolecarbonyl chloride 0.2 g (3.8 mmol) 1-(5-Difluoromethoxy-1-methyl-3-pyrazolyl)-5-methyl-4-pyrazolecarboxylic acid was suspended in 30 ml 1,2-dichloroethane and 1.19 g (10.0 mmol) thionyl chloride was added at room temperature, dropwise. The mixture was heated for 1 hour under reflux and concentrated.

Yield: 0.98 g=100% of theory 4. 1-(5-Difluoromethoxy-1-methyl-3-pyrazolyl)-5-methyl-4-pyrazolecarboxylic acid A mixture of 1.25 g (4.16 mmol) Ethyl 1-(5-difluoromethoxy-1-methyl-3-pyrazolyl)-5-methyl-4-pyrazolecarboxylate, 20 ml ethanol and 0.97 ml aqueous sodium hydroxide (45%) was stirred for 1 hour at 80° C. The reaction solution was concentrated to a half and acidified with hydrochloric acid (37%). The precipitate was suction filtered off, washed with water and dried.

Yield: 1.05 g=93% of theory; mp: 205°–207° C.

5. Ethyl 1-(5-difluoromethoxy-1-methyl-3-pyrazolyl)-5-methyl-4-pyrazolecarboxylate 3.0 g (16.8 mmol) 5-Difluoromethoxy-3-hydrazino-1-methylpyrazole was added to 25 ml ethanol and treated dropwise with 2.96 g (16.0 mmol) ethyl dimethylaminomethylenacetate dissolved in 25 ml ethanol. The mixture was heated under reflux for 2 hours. After cooling the precipitate was suction filtered off.

Yield: 2.52 g=53% of theory; mp: 100° C.

Further starting materials were prepared as follows:

1. 1,1,7-Trichloro-1-hepten-3-one 100 g (0.62 mol) 5-Chlorovaleroyl chloride was added dropwise to 78.53 g (0.589 mmol) aluminium chloride in 150 ml methylene chloride at room temperature. After stirring for 1 hour, 45 ml (0.558 mol) 1,1-dichloroethylene in 25 ml methylene chloride was added dropwise. Under ice-cooling 100 ml water was added dropwise and solid material suction filtered on Celite. The filtrate was washed with water and the organic phase dried and concentrated. The residue was distilled in a rotary evaporator.

Yield: 112.76 g=93.8% of theory. b.p.: 125° C./0.4 mbar 2. 2-Hydrazino-4,5,6,7-tetrahydropyrazolo[1,5-a]pyridine 261.9 ml (5.4 mol) Hydrazine hydrate was added dropwise to 116.6 g (0.54 mol) 1,1,7-trichloro-1-hepten-3-one in 2000 ml 2-propanol at −2° C. (acetone/dry-ice). After stirring for 12 hours at room temperature 60.6 g (1,08 mmol) potassium hydroxide was added and the mixture heated for 5 hours under reflux. The reaction mixture was evaporated to dryness and the residue treated with 100 ml water and 100 ml brine. It was extracted 9 times with ethyl acetate and the and the organic phase washed with brine, dried over sodium sulfate and concentrated.

Yield: 29.29 g=35.6% of theory. Yellow oil 3. 5-Amino-4-cyano-1-(1-methyl-5-methylmercapto-3-pyrazolyl)pyrazole A mixture of 2.0 g (13.1 mmol) 3-Hydrazino-1-methyl-5-methylmercaptopyrazole and 1.8 g (14.4 mmol) ethoxymethylenemalononitrile in 25 ml ethanol was stirred for 30 minutes at room temperature and heated at boiling point for 3 hours. The reaction mixture was concentrated and the residue purified by silica gel chromatography (hexane/ethyl acetate 1:1).

Yield 2.8 g=91% of theory. mp: 165°–166° C.

4. 3-Hydrazino-1-methyl-5-methylmercaptopyrazole 1.1 g (15.8 mmol) sodium nitrite in 4 ml water was added dropwise to 1.9 g (13.1 mmol) 3-amino-1-methyl-5-methylmercaptopyrazole in 28 ml concentrated hydrochloric acid at 0° C. and the mixture stirred for 2 hours at 0° C. Then, at −30° C., a solution of 7.4 g (32.8 mmol) $SnCl_2.2H_2O$ in 5.5 ml concentrated hydrochloric acid was added dropwise and the mixture stirred for 3 hours at this temperature. The reaction mixture was then made basic with 32% caustic soda and extracted with methylene chloride. The organic phase was dried over sodium sulfate and concentrated. 2.0 g of product was obtained which was used without further purification.

5. 3-Amino-1-methyl-5-methylmercaptopyrazole 5.55 g (33.0 mmol) 3-amino-4-cyano-1-methyl-5-methylmercaptopyrazole heated with 50 ml 32% caustic soda at boiling for 24 hours. The reaction mixture was cooled, made slightly acidic with aqueous sodium hydrogen phosphate, heated for 8 hours at 50° C. and extracted with ethyl acetate. The organic phase was dried over sodium sulfate, concentrated and the residue purified by silica gel chromatography (hexane/ethyl acetate 1:1).

Yield: 19 g=398% of theory. mp: 164°–166° C.

6. 3-Amino-4-cyano-1-methyl-5-methylmercaptopyrazole 9.63 g (56.6 mmol) [Bis(methylmercapto)methylene]-malononitrile was suspended in 50 ml water and treated with 3.7 ml (67.9 mmol) methylhydrazine. The mixture was heated at boiling for 1 hour, the reaction solution cooled, the precipitate suction filtered and recrystallised from ethanol.

Yield: 6.5 g=68.% of theory. mp: 120°–121° C.

7. 5-Amino-1-(4,5,6,7-tetrahydropyrazolo-[1,5-a]pyridin-2-yl)-4-pyrazolecarboxylic acid and 2-hydrazino-4,5,6,7-tetrahydro-pyrazolo[1,5-a]pyridine These were prepared according to known methods as follows:

a) 2-Amino-4,5,6,7-tetrahydropyrazolo[1,5-a]pyridine

A solution of 8.19 g (146 mmol) potassium hydroxide in 122 ml water and 122 ml ethanol was added to 19.19 g (292 mmol) hydroxylamine hydrochloride in 200 ml ethanol. The mixture was stirred for 15 minutes, 12.5 g (58 mmol) 2-(2,5-dimethyl-1-pyrrolyl)-4,5,6-7-tetrahydropyrazolo[1,5-a]pyridine added and the mixture heated under reflux for 30 hours. After distilling the ethanol, the mixture was treated with ethyl acetate, solid material filtered off, the aqueous phase saturated with sodium chloride and extracted with ethyl acetate. The organic phase was washed with saturated aqueous sodium chloride, dried over sodium sulfate and concentrated. The crude product was purified by silica gel chromatography (ethyl acetate/methanol).

Yield: 6.12 g=77% of theory; $^1$H NMR ($CDCl_3$, 300 MHz): δ=1.75–1.85 (m,2H), 1.95–2.05(m,2H) 2.68(t,2H,J=7.5 Hz), 3.5(s(wide),2H), 3.92(t,2H,J=7.5 Hz), 5.33(s,1H)

b) 2-(2,5-Dimethyl-1-pyrrolyl)-4,5,6,7-tetrahydropyrazolo[1,5-a]pyridine 16 g (92 mmol) diethyl azodicarboxylate was added dropwise to 19.7 g (84 mmol) 3(5)-(4-hydroxybutyl)-5(3)-(2,5-dimethyl-1-pyrrolyl)pyrazole and 22.1 g (84 mmol) triphenylphosphine in 300 ml tetrahydrofuran under ice cooling. The mixture was stirred for 4 hours at room temperature. It was then concentrated and the residue purified by silica gel chromatography (hexane/ethyl acetate).

Yield: 14.27 g=79% of theory; $n_D^{20}$: 1.5630 c) 3(5)-(4-Hydroxybutyl)-5(3)-(2,5-dimethyl-1-pyrrolyl)pyrazole

A mixture of 18 g (116 mmol) 3(5)-amino-5(3)-(hydroxybutyl)pyrazole, 14.6 g (128 mmol) 2,5-hexanedione and 3.2 ml acetic acid in 100 ml toluene was heated under reflux with removal of water for 8 hours. The resulting precipitate was suction filtered, washed with toluene and dried.

Yield: 19.7 g=72% of theory; mp: 147°–148° C.

d) 3(5)-Amino-5(3)-(hydroxybutyl)pyrazole 4,8 ml Hydrazine monohydrate was added to a solution of 12.3 g (0.1 mol) tetrahydro-2H-pyran-2-ylidenacetonitrile in 100 ml toluene at room temperature and the mixture heated under reflux for 5 hours. A dark yellow oil separated. The reaction mixture was concentrated and the residue purified by silica gel chromatography (ethyl acetate/methanol).

Yield: 11 g=71% of theory

In a similar manner to that described in the previous Examples, the following compounds were prepared.

General formula

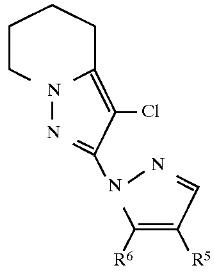

| Compound No. | $R^5$ | $R^6$ | Physical mp[°C.] | Constant $n_D^{20}$ |
|---|---|---|---|---|
| 1.3 | H | H | 80–82 | |
| 1.4 | —CN | H | 120–121 | |
| 1.5 | H | $-NHCOC_2H_5$ | 149–151 | |
| 1.6 | —CN | $-NHCH_3$ | 174–175 | |

-continued

General formula

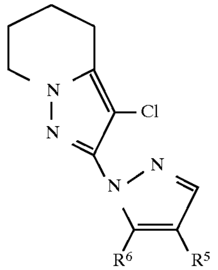

| Compound No. | $R^5$ | $R^6$ | Physical mp[°C.] | Constant $n_D^{20}$ |
|---|---|---|---|---|
| 1.7 | —CN | $-N(CH_3)_2$ | 138–139 | |
| 1.8 | —CN | $-N(C_2H_5)_2$ | | 1.5432 |
| 1.9 | —CN | $-NHCOCH_2Cl$ | 209–211 | |
| 1.10 | —CN | $-N(CH_3)COCH_2Cl$ | 109–110 | |
| 1.11 | —CN | 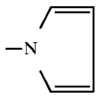 | 131–132 | |
| 1.12 | $-NO_2$ | $-N(C_2H_5)_2$ | 55–57 | |
| 1.13 | $-NO_2$ | $-NHCH_3$ | 184–185 | |
| 1.14 | —CN | Cl | 176–177 | |
| 1.15 | —CN | Br | 196–198 | |
| 1.16 | $-NO_2$ | Cl | | |
| 1.17 | $-NO_2$ | Br | | |
| 1.18 | —CN | $-CH_3$ | 168–171 | |
| 1.19 | —CN | $-C_2H_5$ | | |
| 1.20 | —CN | $-C_3H_7$ | | |
| 1.21 | $-NO_2$ | $-CH_3$ | | |
| 1.22 | $-NO_2$ | $-C_2H_5$ | | |
| 1.23 | $-NO_2$ | $-C_3H_7$ | | |
| 1.24 | —CN | $-OCH_3$ | | |
| 1.25 | —CN | $-OC_2H_5$ | | |
| 1.26 | $-NO_2$ | $-OCH_3$ | | |
| 1.27 | $-NO_2$ | $-OC_2H_5$ | | |
| 1.28 | $-NO_2$ | $-OCH(CH_3)CO_2CH_3$ | | |
| 1.29 | $-NO_2$ | $-OCH(CH_3)CO_2C_2H_5$ | | |
| 1.30 | $-NO_2$ | $-SCH_3$ | | |
| 1.31 | $-NO_2$ | $-SOCH_3$ | | |
| 1.32 | $-NO_2$ | $-SO_2CH_3$ | | |
| 1.33 | $-NO_2$ | $-SC_2H_5$ | | |
| 1.34 | —CN | $-SCH_2COOEt$ | | |
| 1.35 | $-NO_2$ | $-SCH_2COOEt$ | | |
| 1.36 | —CN | $-NHCO(CH_2)_2Cl$ | 149–150 | |
| 1.37 | —CN | $-NHCO(CH_2)_3Cl$ | 119–121 | |

General formula

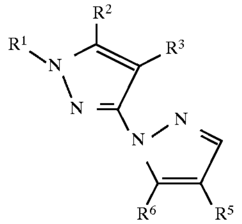

| Compound No. | $R^1$ | $R^2$ | $R^3$ | $R^5$ | $R^6$ | Physical Constant mp [°C.] | $n_D^{20}$ |
|---|---|---|---|---|---|---|---|
| 2.2 | $CH_3$ | $-OCH_3$ | Cl | $-NO_2$ | $-NHCOCH_3$ | 46–48 | |
| 2.3 | $CH_3$ | $-OCHF_2$ | H | H | $-NHCOCF_3$ | 67–70 | |
| 2.4 | $CH_3$ | $-OCHF_2$ | H | H | $-N(CH_3)COCH_3$ | 66 | |
| 2.5 | $CH_3$ | $-OCHF_2$ | H | $-NO_2$ | $-NHCOCH_3$ | 115–116 | |
| 2.6 | $CH_3$ | $-OCHF_2$ | Cl | H | $-NHCOCH_3$ | 106 | |
| 2.7 | $CH_3$ | $-OCHF_2$ | Cl | H | $-NHCOC_2H_5$ | 114–119 | |
| 2.8 | $CH_3$ | $-OCHF_2$ | Cl | H | $-NHCOC_3H_7$ | 80–84 | |
| 2.9 | $CH_3$ | $-OCHF_2$ | Cl | H | $-NHCOCH_2Cl$ | 111–115 | |
| 2.10 | $CH_3$ | $-OCHF_2$ | Cl | H | 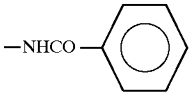 | 152–156 | |
| 2.11 | $CH_3$ | $-OCHF_2$ | Cl | $-NO_2$ | $-NHCOC_2H_5$ | 109–110 | |
| 2.12 | $CH_3$ | $-OCHF_2$ | Cl | $-NO_2$ | $-NHCOC_3H_7$ | 92–96 | |
| 2.13 | $CH_3$ | $-OCHF_2$ | Cl | $-NO_2$ | $-NHCOCH_2Cl$ | 118–120 | |
| 2.14 | $CH_3$ | $-OCHF_2$ | Cl | $-NO_2$ | 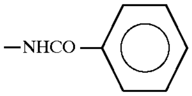 | 194–196 | |
| 2.15 | $CH_3$ | $-OCHF_2$ | Cl | $-NO_2$ | $-NHCH_3$ | 102–105 | |
| 2.16 | $CH_3$ | $-OCHF_2$ | Cl | $-NO_2$ | $-N(CH_3)_2$ | | 1.5564 |
| 2.17 | $-(CH_2)_4-$ | | Cl | $-NO_2$ | $-NHCOCH_3$ | 162 (dec) | |
| 2.18 | $-(CH_2)_4-$ | | Cl | $-NO_2$ | $-NHCOC_3H-$ | 58–61 | |
| 2.19 | $-(CH_2)_4-$ | | Cl | $-NO_2$ | 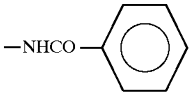 | 168(dec) | |
| 2.20 | $CH_3$ | $-OCHF_2$ | Cl | H | $-NHCO_2C_2H_5$ | 144–146 | |
| 2.21 | $CH_3$ | $-OCHF_2$ | Cl | H | $-NHCONH_2$ | | |
| 2.22 | $CH_3$ | $-OCHF_2$ | Cl | H | $-NHCONHCH_3$ | | |
| 2.23 | $CH_3$ | $-OCHF_2$ | Cl | H | $-NHCON(CH_3)_2$ | | |
| 2.24 | $CH_3$ | $-OCHF_2$ | Cl | $-NO_2$ | $-NHCO_2C_2H_5$ | | 1.5337 |
| 2.25 | $CH_3$ | $-OCHF_2$ | Cl | $-NO_2$ | $-NHCONH_2$ | | |
| 2.26 | $CH_3$ | $-OCHF_2$ | Cl | $-NO_2$ | $-NHCONHCH_3$ | | |
| 2.27 | $CH_3$ | $-OCHF_2$ | Cl | $-NO_2$ | $-NHCON(CH_3)_2$ | | |
| 2.28 | $-(CH_2)_4-$ | | Cl | $-NO_2$ | $-NHCO_2C_2H_5$ | | |
| 2.29 | $-(CH_2)_4-$ | | Cl | $-NO_2$ | $-NHCONH_2$ | | |
| 2.30 | $-(CH_2)_4-$ | | Cl | $-NO_2$ | $-NHCONHCH_3$ | | |
| 2.31 | $-(CH_2)_4-$ | | Cl | $-NO_2$ | $-NHCON(CH_3)_2$ | | |
| 2.32 | $CH_3$ | $-OCHF_2$ | Cl | $-NO_2$ | $-OCH_3$ | | |
| 2.33 | $CH_3$ | $-OCHF_2$ | Cl | $-NO_2$ | $-OC_2H_5$ | | |
| 2.34 | $CH_3$ | $-OCHF_2$ | Cl | $-NO_2$ | $-OCH(CH_3)CO_2C_2H_5$ | | |
| 2.35 | $CH_3$ | $-OCHF_2$ | Cl | $-NO_2$ | $-SCH_3$ | | |
| 2.36 | $CH_3$ | $-OCHF_2$ | Cl | $-NO_2$ | $-SOCH_3$ | | |
| 2.37 | $CH_3$ | $-OCHF_2$ | Cl | $-NO_2$ | $-SO_2CH_3$ | | |
| 2.38 | $-(CH_2)_4-$ | | Cl | $-NO_2$ | $-NHCOCF_3$ | 56–60 | |
| 2.39 | $CH_3$ | $-OCHF_2$ | Cl | $-NO_2$ | 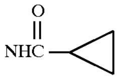 | 44–48 | |
| 2.40 | $CH_3$ | $-OCHF_2$ | Cl | $-NO_2$ | 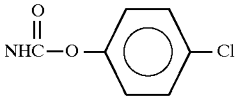 | | 1.5725 |

-continued

General formula

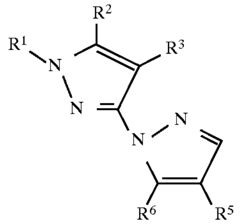

| Compound No. | $R^1$ | $R^2$ | $R^3$ | $R^5$ | $R^6$ | Physical Constant mp [°C.] | $n_D^{20}$ |
|---|---|---|---|---|---|---|---|
| 2.41 | $CH_3$ | $-OCHF_2$ | Cl | $-NO_2$ | 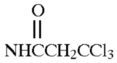 | 47–51 | |
| 2.42 | $CH_3$ | $-OCHF_2$ | Cl | H | 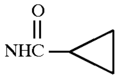 | 122–124 | |

-continued

General formula

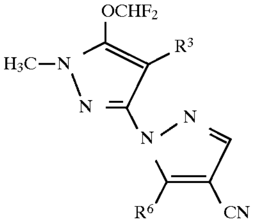

| Example No. | $R^3$ | $R^6$ | Physical mp [°C.] | Constant $n_D$ |
|---|---|---|---|---|
| 2.43 | Cl | $CH_2OCH_2CO_2Me$ | | 1.51438 |
| 2.44 | Cl | 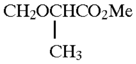 | | 1.50800 |
| 2.45 | Cl | 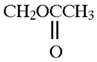 | | 1.51254 |
| 2.46 | Cl | $CH_2SCH_3$ | | 1.54268 |
| 2.47 | Cl | $CH_2SEt$ | | 1.53566 |
| 2.48 | Cl | 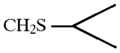 | 74 | |
| 2.49 | Cl | $CH_2SCH_2CO_2Et$ | | 1.52740 |
| 2.50 | Cl | $CH_2NH_2$ | | 1.53932 |
| 2.51 | Cl | $CH_2NHMe$ | | |
| 2.52 | Cl | $CH_2NHEt$ | | |
| 2.53 | Cl | 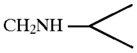 | | 1.51362 |
| 2.54 | Cl | $CH_2NMe_2$ | | |
| 2.55 | Cl | $CH_2NEt_2$ | | |
| 2.56 | Cl | $CH_2N\ prop_2$ | | |
| 2.57 | Cl | $CH_2OCH_2Cl$ | | |
| 2.58 | Cl | $CH_2OCH_2CN$ | | |
| 2.59 | Cl | $CH_2OCH_2-C\equiv CH$ | | |

-continued

General formula

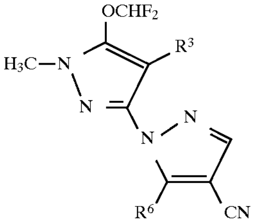

| Example No. | $R^3$ | $R^6$ | Physical mp [°C.] | Constant $n_D$ |
|---|---|---|---|---|
| 2.60 | Cl | 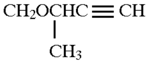 | | |
| 2.61 | Cl | 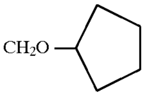 | | |
| 2.62 | Cl | $CH_2OCH_2CO_2Et$ | | |
| 2.63 | Cl | 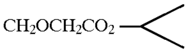 | | |
| 2.64 | Cl | 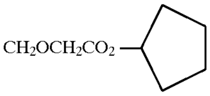 | | |
| 4.6 | Cl | $CH_3$ | 69–70 | |
| 4.7 | Br | $CH_3$ | 76–78 | |
| 4.8 | Cl | $CF_3$ | 90–93 | |
| 4.9 | Br | $CF_3$ | 83–86 | |
| 4.10 | Cl | $C_2H5$ | 74–76 | |
| 4.11 | Cl | $C(CH_3)_3$ | 57–60 | |
| 4.12 | Cl | $CH_2OCH_3$ | | 1.50852 (20° C.) |
| 4.13 | Br | $CH_2OCH_3$ | | 1.52580 |
| 4.14 | Cl | 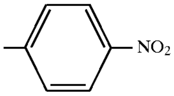 | 118–122 | |

-continued

General formula

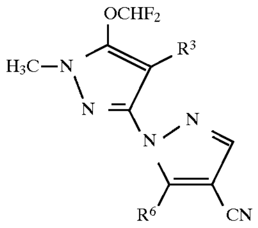

| Example No. | $R^3$ | $R^6$ | Physical mp [°C.] | Constant $n_D$ |
|---|---|---|---|---|
| 4.15 | Cl | $CH_2OH$ | 64 | |
| 4.16 | Cl | $CH_2Cl$ | 54 | |
| 4.17 | Cl | $CH_2Br$ | 52 | |
| 4.18 | Cl | $CH_2OEt$ | 67 | |
| 4.19 | Cl | $CH_2Oprop$ | 48 | |
| 4.20 | Cl | 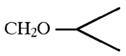 | | 1.50778 (20° C.) |
| 4.21 | Cl | $CH_2O(CH_2)_3CH_3$ | | 1.50450 (20° C.) |

General formula

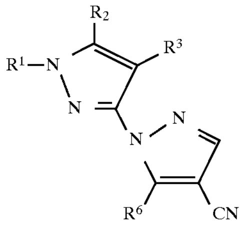

| Example No. | $R^1$ | $R^2$ | $R^3$ | $R^6$ | Physical Constant mp.: [°C.] | $n_D$ |
|---|---|---|---|---|---|---|
| 4.22 | $-(CH_2)_4-$ | | Br | Br | 204–205 | |
| 4.23 | $CH_3$ | $OCHF_2$ | Cl | Br | 71–74 | |
| 4.24 | $CH_3$ | $OCHF_2$ | Cl | Cl | | 1.54046 (20.2° C.) |
| 4.25 | $CH_3$ | $OCHF_2$ | Br | Br | 96–97 | |

General formula

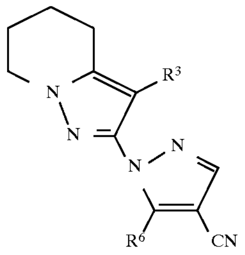

| Example No. | $R^3$ | $R^6$ | Physical Constant mp: [°C.] | $n_D$ |
|---|---|---|---|---|
| 4.26 | Cl | $CF_3$ | 109–110 | |
| 4.27 | Cl | $C_2H_5$ | 130–131 | |
| 4.28 | Cl | $C_2F_5$ | 135.5–136 | |

-continued

General formula

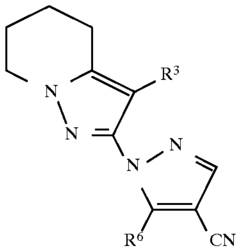

| Example No. | $R^3$ | $R^6$ | Physical Constant mp: [°C.] | $n_D$ |
|---|---|---|---|---|
| 4.29 | Cl | $C_3H_7$ | 62–63 | |
| 4.30 | Cl | $CH(CH_3)_2$ | 107–108 | |
| 4.31 | Cl | Ph | 153–154 | |
| 4.32 | Cl | $CH_2OCH_3$ | 84–85 | |
| 4.33 | Br | $CH_2OCH_3$ | 80–83 | |
| 4.34 | Cl | $CH_2OC_2H_5$ | 73–74 | |
| 4.35 | Cl | $CH_2OC_3H_7$ | 88–89 | |
| 4.36 | Cl | $CH_2OCH(CH_3)_2$ | | 1.5440 (20.1° C.) |
| 4.37 | Cl | $CH_2OH$ | 106–107 | |
| 4.38 | Cl | $CH_2Br$ | 128–129 | |
| 4.39 | Cl | $CH_2OCH_2C{\equiv}CH$ | | 1.5591 (21.2° C.) |
| 4.40 | Cl | $CH_2OCH_2CH{=}CH_2$ | 100.5–102 | |
| 4.41 | Cl | $CH_2OCH_2CH_2OCH_3$ | | 1.5492 (20.2° C.) |
| 4.42 | Cl | $CH_2OCOCH_3$ | 102.5–103 | |
| 4.43 | Cl | $CH_2OCH_2COOH$ | 108–110 | |
| 4.44 | Cl | $CH_2OCH_2COOCH_3$ | | 1.5376 (20° C.) |
| 4.45 | Cl | 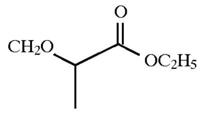 | | 1.5462 (20.1° C.) |
| 4.46 | Cl | 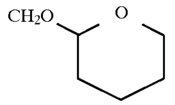 | | 1.5424 (21° C.) |
| 4.47 | Cl | 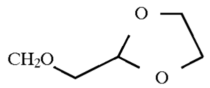 | | 1.5500 (20° C.) |
| 4.48 | Cl | 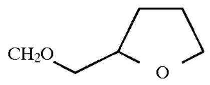 | | 1.5481 (20.2° C.) |
| 4.49 | Cl | $CH_2N(C_2H_5)_2$ | | 1.5377 (20° C.) |
| 4.50 | Cl | $CH_2SCH_3$ | 100–101 | |
| 4.51 | Cl | $CH_2SO_2CH_3$ | 139.5–141 | |
| 4.52 | Cl | $CH_2SOCH_3$ | | 1.5716 (20.4° C.) |
| 4.53 | Cl | $CH_2SCOOH$ | 120 | |
| 4.54 | Cl | $CH_2SCH_2COOC_2H_5$ | | 1.5641 (20° C.) |
| 4.55 | Cl | COOH | 184 | |
| 4.56 | Cl | $CON(C_2H_5)_2$ | 126.5–128 | |

General formula

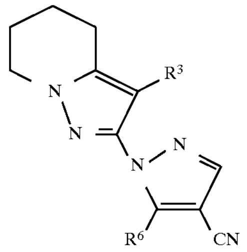

| Example No. | $R^3$ | $R^6$ | Physical Constant mp: [°C.] | $n_D$ |
|---|---|---|---|---|
| 4.57 | Cl | $NHC_3H_7$ | 137 | |
| 4.58 | Cl | $NHCH(CH_3)_2$ | 114 | |
| 4.59 | Cl | $NH(CH_2-CH=CH_2)$ | 125 | |
| 4.60 | Cl | $NHC_4H_9$ | 118 | |
| 4.61 | Cl | $NH[CH(CH_3)CH_2CH_3]$ | 106 | |
| 4.62 | Cl | $NH[CH(CH_3)CH(CH_3)_2]$ | 89–92 | |
| 4.63 | Cl | $NHCH_2CH_2OCH_3$ | 129 | |
| 4.64 | Cl | $NHCH_2CH_2OC_2H_5$ | 111–112 | |
| 4.65 | Cl | $NHCH(CH_3)CH_2OCH_3$ | 105–106 | |
| 4.66 | Cl | $NHCH_2CH_2N(CH_3)_2$ | 131–132 | |
| 4.67 | Cl | $N(CH_3)CH_2CH_2N(CH_3)_2$ | | 1.5621 (20° C.) |
| 4.68 | Cl | $NHCH_2Ph$ | 116 | |
| 4.69 | Cl | 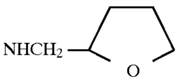 | 122–123 | |
| 4.70 | Br | $N(CH_3)C_2H_5$ | 74–76 | |
| 4.71 | Br | $N(CH_3)C_3H_7$ | 93–95 | |
| 4.72 | Cl | $N(CH_3)CH(CH_3)_2$ | 74 | |
| 4.73 | Cl | $N(CH_3)CH_2-C\equiv CH$ | 91 | |
| 4.74 | Br | $N(CH_3)CH_2-C\equiv CH$ | 112–114 | |
| 4.75 | Cl | $N(C_2H_5)CH_2-C=CH_2$ | 75 | |
| 4.76 | Cl | $N(C_2H_5)CH_2-C\equiv CH$ | | 1.5642 (21.5° C.) |
| 4.77 | Cl | $N(C_3H_7)_2$ | | 1.5468 (23.8° C.) |
| 4.78 | Cl | 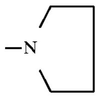 | 156 | |
| 4.79 | Cl | 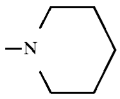 | 84 | |
| 4.80 | Cl | 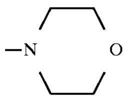 | 107 | |
| 4.81 | Cl | CN | 123 | |
| 4.82 | Cl | $N(C_2H_5)CH_2CH_2N(CH_3)_2$ | | 1.5559 (20° C.) |
| 4.83 | Cl | $N(CH_2-CH=CH_2)_2$ | 79 | |
| 4.84 | Cl | 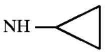 | 145 | |
| 4.85 | Cl | $NHCH_2-C\equiv CH$ | 145 | |
| 4.86 | Cl | $NHCH(C_2H_5)_2$ | 96 | |

-continued

General formula

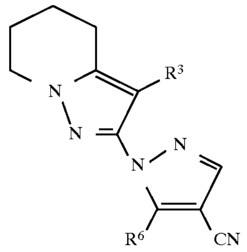

| Example No. | $R^3$ | $R^6$ | Physical Constant mp: [°C.] | $n_D$ |
|---|---|---|---|---|
| 4.87 | Cl | 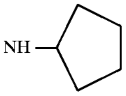 | 139–142 | |
| 4.88 | Cl | 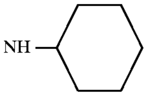 | 141 | |
| 4.89 | Cl | $NHCH_2CH_2N(C_2H_5)_2$ | 78–80 | |
| 4.90 | Cl | $NHCH_2CH_2OH$ | 138 | |
| 4.91 | Cl | $NHCH_2CH_2OCOCH_3$ | 99 | |
| 4.92 | Cl | $NHCH_2CH_2Cl$ | 158 | |
| 4.93 | Cl | $NH(CH_2)_3OCH_3$ | 112 | |
| 4.94 | Cl | $NHCH_2CH_2OCH_2CH_2OH$ | 82–84 | |
| 4.95 | Cl | $NHCH_2CH(OCH_3)_2$ | 127–129 | |
| 4.96 | Cl | $NHCH(CH_3)CH(OCH_3)_2$ | 151 | |
| 4.97 | Cl | $NHCH_2CH(OC_2H_5)_2$ | 111–113 | |
| 4.98 | Cl | 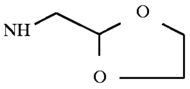 | 115–117 | |
| 4.99 | Cl | 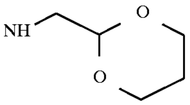 | 121–123 | |
| 4.100 | Cl | 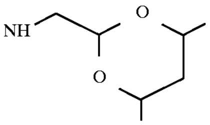 | 149–151 | |
| 4.101 | Cl | 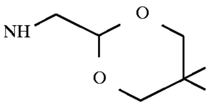 | 114.5–117 | |
| 4.102 | Cl | $NHCH_2CH_2SC_2H_5$ | 113–115 | |
| 4.103 | Cl | 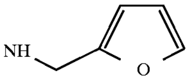 | 170 | |
| 4.104 | Cl | 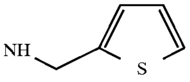 | 129–131 | |
| 4.105 | Cl | $NHCH_2COOC_2H_5$ | 162 | |
| 4.106 | Cl | 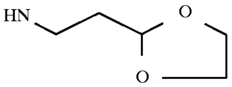 | | |

-continued
General formula
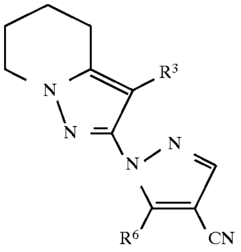
| Example No. | $R^3$ | $R^6$ | Physical Constant mp: [°C.] | $n_D$ |
|---|---|---|---|---|
| 4.107 | Cl | 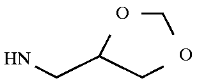 | | |
| 4.108 | Cl | 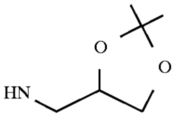 | | |
| 4.109 | Cl | 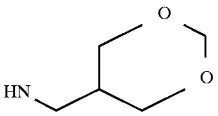 | | |
| 4.110 | Cl | 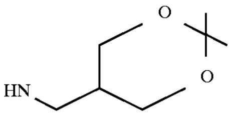 | | |
| 4.111 | Cl | 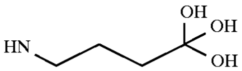 | | |
| 4.112 | Cl | 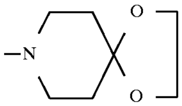 | | |
General formula
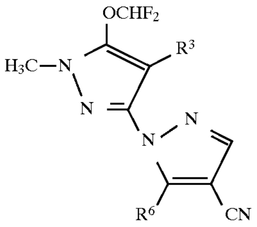
| Example No. | $R^3$ | $R^6$ | Physical Constant mp: [°C.] | $n_D$ |
|---|---|---|---|---|
| 4.113 | Cl | $NHC_3H_7$ | 80 | |
| 4.114 | Cl | 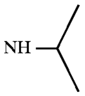 | 77 | |
-continued
General formula
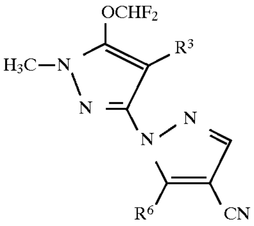
| Example No. | $R^3$ | $R^6$ | Physical Constant mp: [°C.] | $n_D$ |
|---|---|---|---|---|
| 4.115 | Cl | $NH(CH_2)_2OCH_3$ | 78–79 | |
| 4.116 | Cl | $N(CH_3)C_2H_5$ | | 1.52076 (20° C.) |
| 4.117 | Cl | $N(C_2H_5)_2$ | | 1.49924 (20° C.) |
| 4.118 | Cl | $N(CH_3)CH(CH_3)_2$ | | 1.51528 (20° C.) |
| 4.119 | Br | $N(CH_3)CH(CH_3)_2$ | | 1.51258 (20.3° C.) |
| 4.120 | Cl | $N(C_2H_5)CH(CH_3)_2$ | 52 | |
| 4.121 | Cl | $N(C_3H_7)_2$ | | 1.49338 (20° C.) |
| 4.122 | Cl | 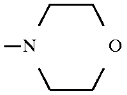 | 100–102 | |
| 4.123 | Br | 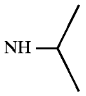 | 70–72 | |
| 4.124 | Cl | 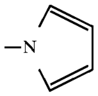 | | 1.53388 (21.6° C.) |

General formula

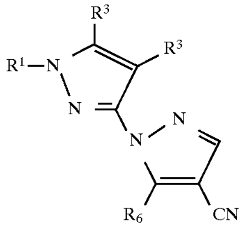

| Example No. | $R^1$ | $R^2$ | $R^3$ | $R^6$ | Physical Constant mp: [°C.] | $n_D$ |
|---|---|---|---|---|---|---|
| 4.125 | $-(CH_2)_4-$ | | Cl | $NHC_2H_5$ | 136 | |
| 4.126 | $CH_3$ | $OCHF_2$ | Cl | $NHCH_3$ | 147–148 | |
| 4.127 | $CH_3$ | $OCHF_2$ | Br | $NHCH_3$ | 150–152 | |
| 4.128 | $CH_3$ | $OCHF_2$ | Br | $NHC_2H_5$ | 96 | |
| 4.129 | $-(CH_2)_4-$ | | Cl | 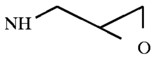 | 133 | |
| 4.130 | $-(CH_2)_4-$ | | Cl | $NHCH_2CN$ | 183 | |
| 4.131 | $-(CH_2)_4-$ | | Cl | $NHCH_2—C\equiv C—CH_3$ | 171.5–173.5 | |
| 4.132 | $-(CH_2)_4-$ | | Cl | $NHCH_2C\equiv C—CH_3$ | | |
| 4.133 | $-(CH_2)_4-$ | | Cl | $NHCH_2—C\equiv C—C_2H_5$ | | |
| 4.134 | $-(CH_2)_4-$ | | Cl | $NHCH_2—C\equiv C—CH_2—OCH_3$ | | |

General formula

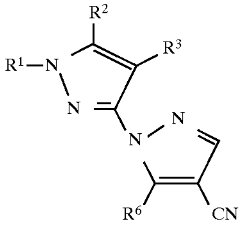

| Example No. | $R^1$ | $R^2$ | $R^3$ | $R^6$ | Physical Constant mp: [°C.] | $n_D$ |
|---|---|---|---|---|---|---|
| 4.135 | $-(CH_2)_4-$ | | Cl | $N(CH_3)C_2H_5$ | 69 | |
| 4.136 | $-(CH_2)_4-$ | | Cl | $N(CH_3)C_3H_7$ | 89 | |
| 4.137 | $-(CH_2)_4-$ | | Cl | $N(CH_3)C_4H_9$ | 72 | |
| 4.138 | $-(CH_2)_4-$ | | Cl | $N(CH_3)CH(CH_3)C_2H_5$ | 68 | |
| 4.139 | $-(CH_2)_4-$ | | Cl | $N(CH_3)CH(CH_3)CH(CH_3)_2$ | 70 | |
| 4.140 | $-(CH_2)_4-$ | | Cl | $N(CH_3)CH_2CH_2OCH_3$ | 80 | |
| 4.141 | $-(CH_2)_4-$ | | Cl | $N(C_2H_5)C_3H_7$ | 92 | |
| 4.142 | $-(CH_2)_4-$ | | Cl | $N(C_2H_5)C_4H_9$ | | 1.5471 (22.9° C.) |
| 4.143 | $-(CH_2)_4-$ | | Cl | $N(C_2H_5)CH(CH_3)C_2H_5$ | 115 | |
| 4.144 | $-(CH_2)_4-$ | | Cl | $N(C_2H_5)CH(CH_3)CH(CH_3)_2$ | 130–133 | |
| 4.145 | $-(CH_2)_4-$ | | Cl | $N(C_2H_5)CH_2CH_2OCH_3$ | 58 | |
| 4.146 | $-(CH_2)_4-$ | | Cl | $N(C_2H_5)CH_2Ph$ | 110 | |
| 4.147 | $-(CH_2)_4-$ | | Cl | $N(CH_3)CH_2CH_2OC_2H_5$ | | 1.5559 (20° C.) |
| 4.148 | $-(CH_2)_4-$ | | Cl | $N(C_2H_5)CH_2CH_2OC_2H_5$ | | 1.5484 (20° C.) |
| 4.149 | $-(CH_2)_4-$ | | Cl | $N(C_3H_7)CH_2CH_2OC_2H_5$ | | 1.5452 (20° C.) |
| 4.150 | $-(CH_2)_4-$ | | Cl | $N(CH_2—C\equiv CH)CH_2CH_2OC_2H_5$ | | 1.55688 (20° C.) |
| 4.151 | $-(CH_2)_4-$ | | Cl | $N(CH_3)CH(CH_3)CH_2OCH_3$ | | 1.55644 (20° C.) |

-continued

General formula

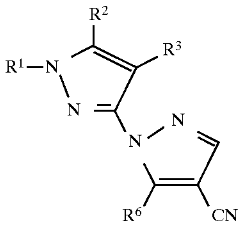

| Example No. | $R^1$ | $R^2$ | $R^3$ | $R^6$ | Physical Constant mp: [°C.] | $n_D$ |
|---|---|---|---|---|---|---|
| 4.152 | $-(CH_2)_4-$ | | Cl | $N(C_2H_5)CH(CH_3)CH_2OCH_3$ | 94–95 | |
| 4.153 | $-(CH_2)_4-$ | | Cl | $N(CH_2-C\equiv CH)CH(CH_3)CH_2OCH_3$ | 124–126 | |
| 4.154 | $CH_3$ | $OCHF_2$ | Cl | $N(C_2H_5)CH_2CH_2OCH_3$ | | 1.51744 (19.9° C.) |
| 4.155 | $CH_3$ | $OCHF_2$ | Cl | $N(CH_2-C\equiv CH)CH_2CH_2OCH_3$ | | 1.51376 (20° C.) |
| 4.156 | $-(CH_2)_4-$ | | Cl | $NH(CH_2-C\equiv CH)$ | 145 | |
| 4.157 | $-(CH_2)_4-$ | | Cl | $N(CH(CH_3)C_2H_5)CH_2-C\equiv CH$ | 142 | |
| 4.158 | $-(CH_2)_4-$ | | Cl | 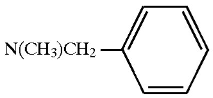 | 108 | |
| 4.159 | $-(CH_2)_4-$ | | Cl | $N(C_2H_5)CH(CH_3)CH_3$ | 106 | |
| 4.160 | $-(CH_2)_4-$ | | Cl | $N(C_2H_5)CH(CH_3)_2$ | 106 | |
| 4.161 | $-(CH_2)_4-$ | | Cl | $N(CH_2-C\equiv CH)CH(CH_3)C_2H_5$ | 142 | |
| 4.162 | $-(CH_2)_4-$ | | Cl | $N(CH_3)CH_2Ph$ | 108 | |
| 4.163 | $-(CH_2)_4-$ | | Cl | $N(CH_3)CH(C_2H_5)_2$ | 110 | |
| 4.164 | $-(CH_2)_4-$ | | Cl | $N(CH_3)CH_2CH(OCH_3)_2$ | 71 | |
| 4.165 | $-(CH_2)_4-$ | | Cl | $N(C_2H_5)CH_2CH(OCH_3)_2$ | | 1.5459 (20° C.) |
| 4.166 | $-(CH_2)_4-$ | | Cl | $N(CH_2-C\equiv CH)CH_2CH(OCH_3)_2$ | 111–113 | |
| 4.167 | $-(CH_2)_4-$ | | Cl | 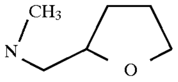 | 97–99 | |
| 4.168 | $-(CH_2)_4-$ | | Cl | 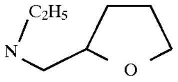 | 169–171 | |
| 4.169 | $-(CH_2)_4-$ | | Cl | 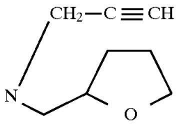 | 140–142 | |
| 4.170 | $-(CH_2)_4-$ | | Cl | $N(CH_3)CH_2CH_2SC_2H_5$ | | 1.5855 (22.4° C.) |
| 4.171 | $-(CH_2)_4-$ | | Cl | $N(CH_3)CH_2-C\equiv C-CH_3$ | | |
| 4.172 | $-(CH_2)_4-$ | | Cl | $N(CH_3)CH_2-C\equiv C-C_2H_5$ | | |
| 4.173 | $-(CH_2)_4-$ | | Cl | $N(CH_3)CH_2-C\equiv C-CH_2-OCH_3$ | | |
| 4.174 | $-(CH_2)_4-$ | | Cl | 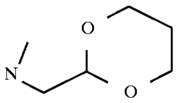 | | |

-continued

General formula

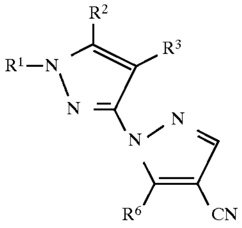

| Example No. | $R^1$ | $R^2$ | $R^3$ | $R^6$ | Physical Constant mp: [°C.] | $n_D$ |
|---|---|---|---|---|---|---|
| 4.175 | $-(CH_2)_4-$ | | Cl | 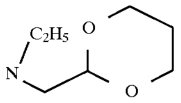 | | |
| 4.176 | $-(CH_2)_4-$ | | Cl | 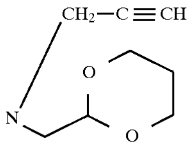 | | |

General formula

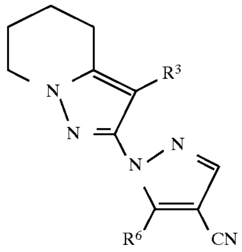

| Example No. | $R^3$ | $R^6$ | Physical Constant mp: [°C.] | $n_D$ |
|---|---|---|---|---|
| 4.177 | Br | $N(C_2H_5)_2$ | 71–72 | |
| 4.178 | Cl | $N(CH_2-C\equiv CH)_2$ | | 1.5739 (22.8° C.) |
| 4.179 | Cl | $N(CH_2CO_2C_2H_5)_2$ | | 1.5427 (20° C.) |
| 4.180 | Cl | 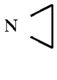 | 108 | |
| 4.181 | Cl | $N(CH_2-C\equiv C-CH_3)_2$ | | |
| 4.182 | Cl | $N(CH_2-C\equiv C-C_2H_5)_2$ | | |
| 4.183 | Cl | $N(CH_2-C\equiv C-CH_2OCH_3)_2$ | | |

General formula

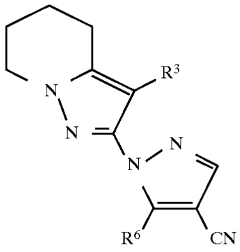

| Example No. | $R_3$ | $R_6$ | Physical Constant mp: [°C.] | $n_D$ |
|---|---|---|---|---|
| 4.184 | Cl | $NHCOCH_3$ | 123 | |
| 4.185 | Cl | $NHCOCF_3$ | 178 | |
| 4.186 | Cl | $NHCOCCl_3$ | 224 | |
| 4.187 | Cl | $NHCOC_2H_5$ | 162 | |
| 4.188 | Cl | $NHCOC_3H_7$ | 152 | |
| 4.189 | Br | $NHCOC_3H_7$ | 148–150 | |
| 4.190 | Cl | 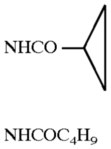 | 171 | |
| 4.191 | Cl | $NHCOC_4H_9$ | 103 | |
| 4.192 | Cl | 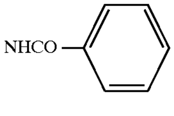 | 252 | |
| 4.193 | Cl | $NHCOCH_2OCH_3$ | 201–203 | |

-continued

General formula

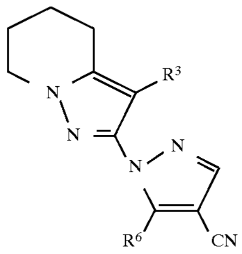

| Example No. | $R_3$ | $R_6$ | Physical Constant mp: [°C.] | $n_D$ |
|---|---|---|---|---|
| 4.194 | Cl | 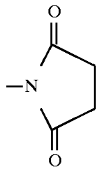 | 185–187 | |
| 4.195 | Cl | 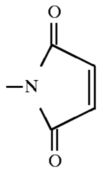 | 165 | |
| 4.196 | Cl | 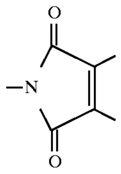 | 151 | |
| 4.197 | Cl | 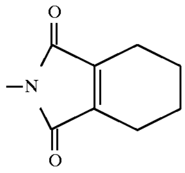 | 75 | |
| 4.198 | Cl | 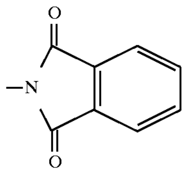 | 185 | |
| 4.199 | Cl | $NHCON(CH_3)_2$ | 168 | |
| 4.200 | Cl | $NHCSN(CH_3)_2$ | 170 | |
| 4.201 | Cl | $NHCON(CH_3)Ph$ | 62–64 | |

General formula

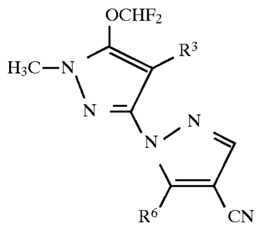

| Example No. | $R^3$ | $R^6$ | Physical Constant mp: [°C.] | $n_D$ |
|---|---|---|---|---|
| 4.202 | Cl | $NHCOCH_2OCCH_3$<br>‖<br>O | 125 | |
| 4.203 | Cl | $NHCH_2CO_2Et$ | 107–109 | |
| 4.204 | Cl | $NHCHCO_2Et$<br>\|<br>$CH_3$ | 111–113 | |
| 4.205 | Cl | $N(Et)COCH_3$ | 78–80 | |
| 4.206 | Cl | $N(Et)COCH_2Cl$ | | 1.53412 |
| 4.207 | Cl | N( 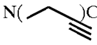 )$COCH_2CH$ | 85–87 | |
| 4.208 | Cl | N(Et)COEt | | 1.51132 |
| 4.209 | Cl | N( 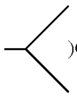 )COEt | | 1.51214 |
| 4.210 | Cl | N( 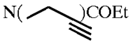 )COEt | | 1.52582 |
| 4.211 | Cl | $N(CH_2CO_2Me)COEt$ | 87–90 | |
| 4.212 | Br | NHCOEt | 120–122 | |
| 4.213 | Br | NHCOnbutyl | 100–104 | |
| 4.214 | Br | $NHCOCH_2OCCH_3$<br>‖<br>O | 103 | |
| 4.215 | Br | $N(COEt)_2$ | 105–107 | |
| 4.216 | Cl | $NHCOCH_3$ | 116–118 | |
| 4.217 | Cl | $NHCOCH_2Cl$ | 135–137 | |
| 4.218 | Cl | $NHCOCF_3$ | 134–137 | |
| 4.219 | Cl | $NHCOC_2H_5$ | 126–128 | |
| 4.220 | Br | $NHCOC_3H_7$ | 141–144 | |
| 4.221 | Cl | $NHCOC_3H_7$ | 140–143 | |
| 4.222 | Cl | NHCO 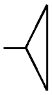 | 96–100 | |
| 4.223 | Cl | $N(COCH_3)_2$ | 117–119 | |
| 4.224 | Cl | $N(COC_2H_5)_2$ | 93–95 | |
| 4.225 | Cl | $N(COC_3H_7)_2$ | 73–76 | |

General formula

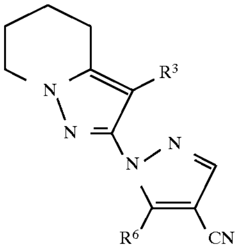

| Example No. | $R^3$ | $R^6$ | Physical Constant mp: [°C.] | $n_D$ |
|---|---|---|---|---|
| 4.226 | Cl | $N(CH_3)COCH_3$ | 121 | |
| 4.227 | Cl | $N(C_2H_5)COCH_3$ | 79 | |
| 4.228 | Cl | $N(C_3H_7)COCH_3$ | 85 | |
| 4.229 | Cl | $(CH_2—C≡CH)COCH_3$ | 06 | |
| 4.230 | Cl | $N(CH_2CH_2OCH_3)COCH_3$ | 128 | |
| 4.231 | Cl | $N(CH_2Ph)COCH_3$ | 111–113 | |
| 4.232 | Cl | $N(C_2H_5)COCH_2Cl$ | 98–101 | |
| 4.233 | Cl | $N(C_3H_7)COCH_2Cl$ | 168 | |
| 4.234 | Cl | $N(CH_2CH_2OCH_3)COCH_2Cl$ | 107 | |
| 4.235 | Cl | $N(CH_2CH_2OC_2H_5)COCH_2Cl$ | | 1.54132 (20° C.) |
| 4.236 | Cl | $N(CH_2Ph)COCH_2Cl$ | 165–168 | |
| 4.237 | Cl | $N(CH_3)COCF_3$ | 98 | |
| 4.238 | Cl | $N(C_2H_5)COCF_3$ | 102 | |
| 4.239 | Cl | $N(CH_2—C≡CH)COCF_3$ | 137 | |
| 4.240 | Cl | $N(CH_3)COC_2H_5$ | 125–128 | |
| 4.241 | Cl | $N(C_2H_5)COC_2H_5$ | 83 | |
| 4.242 | Cl | $N(CH_2CH_2OC_2H_5)COC_2H_5$ | | 1.54132 (20° C.) |
| 4.243 | Cl | $N(CH_3)COC_3H_7$ | 90 | |
| 4.244 | Cl | $N(C_2H_5)COC_3H_7$ | 72 | |
| 4.245 | Br | $N(C_2H_5)COC_3H_7$ | 103–104 | |
| 4.246 | Cl | $N(CH_3)CO$— 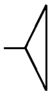 | 121 | |
| 4.247 | Cl | $N(C_2H_5)CO$— 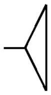 | 122 | |
| 4.248 | Cl | $N(CH_3—C=CH)CO$— 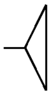 | 191 | |
| 4.249 | Cl | $N(CH_3)COC_4H_9$ | | 1.5427 (23.2° C.) |
| 4.250 | Cl | $N(C_2H_5)COC_4H_9$ | | 1.5386 (23.3° C.) |
| 4.251 | Cl | $N(COCH_3)CH_2OCH_3$ | 109 | |
| 4.252 | Cl | $N[CH(CH_3)_2]COCH_3$ | 112–114 | |
| 4.253 | Cl | $N(CH_2CH_2OC_2H_5)COCH_3$ | 100–103 | |
| 4.254 | Cl | $N[CH(CH_3)CH(CH_3)_2]COCH_3$ | 93 | |
| 4.255 | Cl | $N[CH(CH_3)_2]COCH_2Cl$ | 146–149 | |
| 4.256 | Cl | $N[CH(CH_3)C_2H_5]COCH_2Cl$ | 109–111 | |
| 4.257 | Cl | $N[CH(CH_3)CH_2OCH_3]COCH_2Cl$ | 126 | |
| 4.258 | Cl | $N(CH_2CH_2SC_2H_5)COCH_3$ | | 1.5655 (22.4° C.) |

General formula

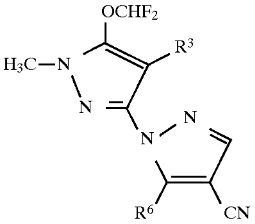

| Example No. | $R^3$ | $R^6$ | Physical Constant mp: [°C.] | $n_D$ |
|---|---|---|---|---|
| 4.259 | Cl | $N(CH_3)COCH_3$ | 108–109 | |
| 4.260 | Cl | $N(CH_3)COCH_2Cl$ | 87–90 | |
| 4.261 | Cl | $N(CH_3)COC_2H_5$ | 63–67 | |
| 4.262 | Cl | $N(C_2H_5)COCH_3$ | 77 | |
| 4.263 | Br | $N(C_2H_5)COC_3H_7$ | 75–77 | |
| 4.264 | Cl | $N(C_3H_7)COCH_3$ | 78–80 | |
| 4.265 | Br | N(Et)COEt | | 1.5168 |
| 4.266 | Br | N( 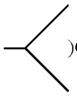 )COEt | | 1.51532 |
| 4.267 | Br | N( 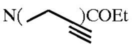 )COEt | | 1.53406 |
| 4.268 | Br | $N(CH_2CN)COEt$ | 95–98 | |
| 4.269 | Br | $N(Me)COC_3H_7$ | | 1.55112 |
| 4.270 | Br | $N(CH_2OCH_3)COC_3H_7$ | | 1.53024 |
| 4.271 | Br | $N(CH_2CO_2Et)COC_3H_7$ | | 1.52918 |

General formula

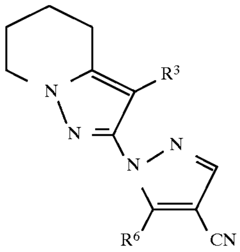

| Example No. | $R^3$ | $R^6$ | Physical Constant mp: [°C.] | $n_D$ |
|---|---|---|---|---|
| 4.272 | Cl | $OCH_3$ | 174–176 | |
| 4.273 | Cl | $OC_2H_5$ | 117–118 | |
| 4.274 | Br | $OC_2H_5$ | 120–122 | |
| 4.275 | Cl | $OC_3H_7$ | 95–96 | |
| 4.276 | Cl | $OCH_2CH_2OCH_3$ | | 1.55562 (20° C.) |
| 4.277 | Cl | $OCH_2CH_2OCH_2CH_2OCH_3$ | | 1.54220 (20° C.) |
| 4.278 | Cl | $OCH_2—C≡CH$ | 123 | |
| 4.279 | Cl | $OC_4H_9$ | 74–76 | |
| 4.280 | Cl | 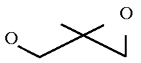 | 99.5–101.5 | |
| 4.281 | Cl | 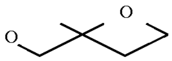 | 102–104 | |

-continued

General formula

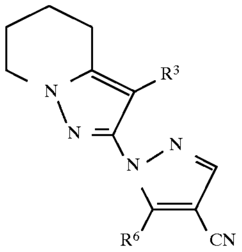

| Example No. | $R^3$ | $R^6$ | Physical Constant mp: [°C.] | $n_D$ |
|---|---|---|---|---|
| 4.282 | Cl | 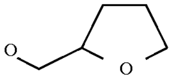 | | 1.5575 (21.8° C.) |
| 4.283 | Cl | 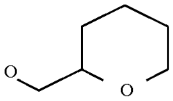 | | 1.5520 (22° C.) |
| 4.284 | Cl | 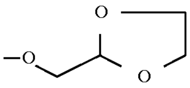 | | 1.5524 (21.8° C.) |
| 4.285 | Cl | 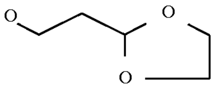 | 67–70 | |
| 4.286 | Cl | $OCH_2CH_2CH(OC_2H_5)_2$ | | 1.5306 (20° C.) |
| 4.287 | Cl | 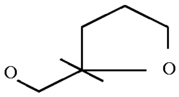 | 91–93 | |
| 4.288 | Cl | 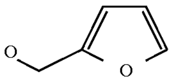 | | 1.5544 (22.7° C.) |
| 4.289 | Cl | $SCH_2COOCH(CH_3)_2$ | 125 | |
| 4.290 | Cl | 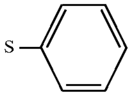 | | 1.6136 (21.5° C.) |
| 4.291 | Cl | $SCH_3$ | 128 | |
| 4.292 | Cl | $SCH_2CH_3$ | 62 | |
| 4.293 | Cl | $SCH(CH_3)_2$ | | 1.5786 (21.8° C.) |
| 4.294 | Cl | $SCH_2-C\equiv CH$ | 94 | |
| 4.295 | Cl | $SCH_2CO_2C_2H_5$ | | 1.5646 (22.5° C.) |
| 4.296 | Cl | $SCH(CH_3)CO_2C_2H_5$ | | 1.5602 (21.8° C.) |
| 4.297 | Cl | $SOCH_3$ | 163 | |
| 4.298 | Cl | $SO_2CH_3$ | 229 | |
| 4.299 | Cl | $OCH_2CH(CH_3)_2$ | 84–87 | |
| 4.300 | Cl | $OCH_2CH(OC_2H_5)_2$ | | 1.5283 (20° C.) |
| 4.301 | Cl | $O(CH_2)_3OCH_3$ | | 1.5482 (20° C.) |
| 4.302 | Cl | $OCH_2Ph$ | 120–122 | |
| 4.303 | Cl | $OCH_2CH_2OCH(CH_3)_2$ | 67–69 | |

-continued

General formula

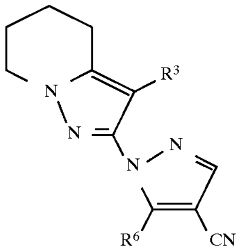

| Example No. | $R^3$ | $R^6$ | Physical Constant mp: [°C.] | $n_D$ |
|---|---|---|---|---|
| 4.304 | Cl | 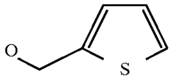 | 149–152 | |
| 4.305 | Cl | $OCH(CH_3)CO_2C_2H_5$ | | |
| 4.306 | Cl | $OCH_2CO_2C_2H_5$ | | |
| 4.307 | Cl | 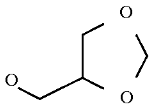 | | |
| 4.308 | Cl | 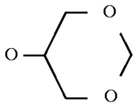 | | |
| 4.309 | Cl | 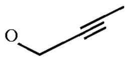 | | |
| 4.310 | Cl | 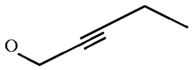 | | |
| 4.311 | Cl | 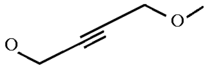 | | |

General formula

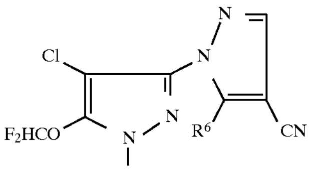

| Example- No. | $R^6$ | Physical Constant mp: [°C.] | $n_D$ |
|---|---|---|---|
| 4.312 | $SCH_2CO_2Et$ | | 1.53242 (20.2° C.) |
| 4.313 | $SCH_3$ | | |
| 4.314 | SEt | | |
| 4.315 | Sprop | | |
| 4.316 | 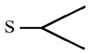 | | |
| 4.317 | S nbutyl | | |

-continued
General formula
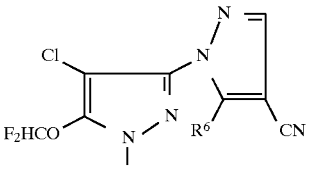
| Example- No. | $R^6$ | Physical Constant mp: [°C.] | $n_D$ |
|---|---|---|---|
| 4.318 | 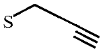 | | |
| 4.319 | 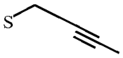 | | |
| 4.320 | $OCH_3$ | | |
| 4.321 | OEt | | |
| 4.322 | O prop | | |
| 4.323 | 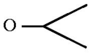 | | |
| 4.324 | O nbutyl | | |
| 4.325 | 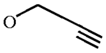 | | |
| 4.326 | 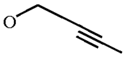 | | |
| 4.327 | 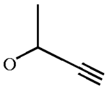 | | |
| 4.328 | 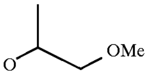 | | |
| 4.329 | 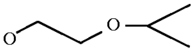 | | |
| 4.330 | 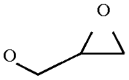 | | |
| 4.331 | 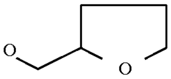 | | |
| 4.332 | 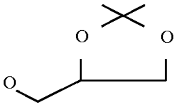 | | |
| 4.333 | 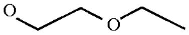 | | |
| 4.334 | 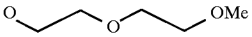 | | |
| 4.335 | 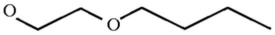 | | |
| 4.336 | 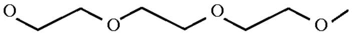 | | |
-continued
General formula
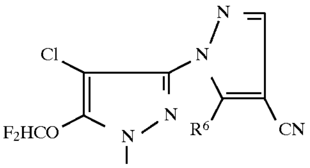
| Example- No. | $R^6$ | Physical Constant mp: [°C.] | $n_D$ |
|---|---|---|---|
| 4.337 | 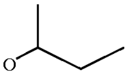 | | |
| 4.338 | 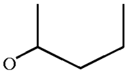 | | |
| 4.339 | 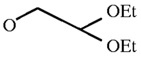 | | |
| 4.340 | 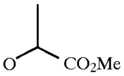 | | |
| 4.341 | 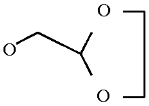 | | |
| 4.342 | 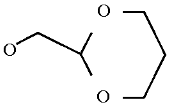 | | |
| 4.343 | 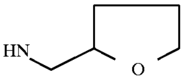 | 98–100 | |
| 4.344 | 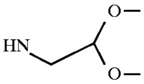 | 103–105 | |
| 4.345 | 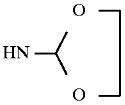 | 93–96 | |
| 4.346 | 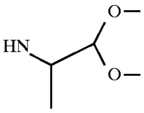 | | |
| 4.347 | 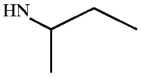 | | 1.51180 |
| 4.348 | 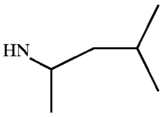 | 101–103 | |
| 4.349 | 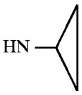 | 105–108 | |

-continued

General formula

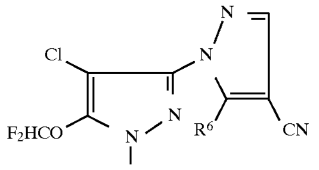

| Example-No. | $R^6$ | Physical Constant mp: [°C.] | $n_D$ |
|---|---|---|---|
| 4.350 | 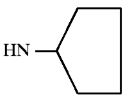 | 96–98 | |
| 4.351 | 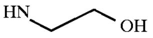 | | |
| 4.352 | 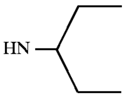 | | |
| 4.353 | 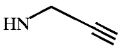 | | |
| 4.354 | 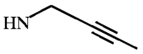 | | |

General formula

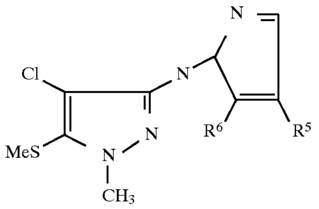

| Example No. | $R^5$ | $R^6$ | Physical Constant mp: [°C.] | $n_D$ |
|---|---|---|---|---|
| 4.355 | CN | $N(C_2H_5)_2$ | 89–90 | |
| 4.356 | CN | 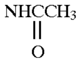 | 123–124 | |
| 4.357 | CN | $CH_3$ | | |
| 4.358 | CN | $CH_2OCH_3$ | | |
| 4.359 | CN | Br | | |
| 4.360 | CN | Cl | | |
| 4.361 | CN | $OCH_2CH_2OCH_3$ | | |
| 4.362 | $NO_2$ | 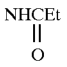 | | |

The following examples illustrate the possibilities for use of the compounds of the invention.

In these Examples, herbicidal activity is denoted on a score of 0 to 4 in which:

0=no damage
1=1–24% damage
2=25–74% damage
3=75–89% damage
4=90–100% damage

The abbreviations used for the various plant species have the following meanings ABUTH=*Abutilon theophrasti* VERPE=*Veronica persica*
AGRRE=*Elymus repens* VIOSS=*Viola sp*
ALOMY=*Alopecurus myosuroides*
AVEFA=*Avena fatua*
BROTE=*Bromus tectorum*
CYPDI=*Cyperus difformis*
CYPES=*Cyperus esculentus*
ECHGH=*Echinochloa crus-galli*
GALAP=*Galium aparine*
GOSHI=*Gossypium hirsutum*
IPOSS=*Ipomea purpurea*
MATCH=*Matricaria chamomilla*
MOOVA=*Monochoria vaginalis*
ORYSA=*Oryza sativa*
PANSS=*Panicum maximum*
PASDS=*Paspalum distichum*
POLSS=*Polygonum sp.*
SCPJU=*Scirpus juncoides*
SEBEX=*Sesbania exaltata*
SETVI=*Setaria viridis*
SORHA=*Sorghum halepense*
SOLSS=*Solanum sp.*

Test Example A

In a greenhouse, the noted plant species were treated pre-emergently with the noted compounds, at a rate of 0.1 kg active ingredient/ha. The compounds were sprayed evenly over the soil as emulsions in 500 liters water/ha. Three weeks after the treatment, the compounds of the invention showed excellent activity against the weeds. The comparison material did not show the same high activity.

| Compounds | ALOMY | AGRRE | AVEFA | BROTE | SETVI | | PANSS | SORHA | CYPES | | ABUTH | IPOSS | MATCH | POLSS | SEBEX | SOLSS | VERPE | VIOSS |
|---|---|---|---|---|---|---|---|---|---|---|---|---|---|---|---|---|---|---|
| Ex. 1.1 | — | — | — | — | 3 | | 3 | 3 | — | | 3 | — | 4 | 2 | 1 | 4 | 3 | 4 |
| Ex. 1.2 | 3 | — | 3 | — | 4 | | 4 | — | — | | 4 | 3 | 4 | 4 | 4 | 4 | 4 | 4 |
| Ex. 1.6 | 3 | 3 | 3 | — | 4 | | 4 | 3 | — | | 4 | — | 4 | 4 | 3 | 4 | 4 | 4 |
| Ex. 1.7 | — | — | — | — | 3 | | 3 | 3 | — | | 4 | — | 4 | 3 | 4 | 4 | 4 | 2 |
| Ex. 1.8 | 2 | — | — | — | 2 | | 2 | 3 | — | | 4 | — | 4 | 4 | 3 | 4 | 3 | 2 |
| Ex. 1.9 | 2 | 2 | 3 | — | 4 | | 3 | 3 | — | | 4 | — | 4 | 3 | 3 | 4 | 4 | 4 |
| Ex. 1.11 | 2 | — | 3 | — | 4 | | 3 | 3 | — | | 3 | — | 4 | 1 | 0 | 4 | 4 | 3 |
| Ex. 1.13 | 3 | — | 3 | — | 4 | | 3 | 4 | 2 | | 4 | — | 4 | 4 | 3 | 4 | 4 | 2 |
| Ex. 1.15 | 3 | 2 | 2 | — | 4 | | 4 | 2 | — | | — | — | 4 | 2 | 2 | 4 | 3 | 4 |
| Ex. 1.18 | 4 | 3 | 3 | — | 4 | | 4 | 4 | 3 | | 4 | — | 4 | 4 | 2 | 4 | 4 | 4 |
| Ex. 2.1 | 3 | 4 | 4 | 4 | 4 | | 4 | 4 | 3 | | 4 | 4 | 4 | 4 | 4 | 4 | 4 | 4 |
| Ex. 2.11 | 3 | — | 3 | — | — | | 4 | 4 | 4 | | 3 | 4 | 4 | 4 | 4 | 4 | 4 | 4 |
| Ex. 2.12 | 3 | — | 3 | — | 4 | | 4 | 4 | — | | 4 | 3 | 4 | 4 | 4 | 4 | 4 | 4 |
| Ex. 2.13 | 3 | — | — | — | 4 | | 4 | 4 | — | | 3 | 3 | 4 | 4 | 4 | 3 | 4 | 4 |
| Ex. 2.17 | 3 | 3 | 3 | — | 4 | | 4 | 4 | — | | 4 | 4 | 4 | 4 | 4 | 4 | 4 | 4 |
| Ex. 2.18 | 3 | — | 3 | — | 4 | | 4 | 3 | — | | 4 | — | 4 | 4 | 2 | 4 | 4 | 4 |
| Ex. 2.24 | 3 | — | 3 | — | 3 | | 3 | 3 | 3 | | 4 | 4 | 3 | 4 | 4 | 4 | 4 | 3 |
| Ex. 2.38 | 3 | — | — | — | 3 | | 3 | — | — | | 4 | 3 | 4 | 3 | 4 | 4 | 4 | 4 |
| Ex. 4.12 | 4 | 4 | 4 | 3 | 4 | 4 | 4 | 3 | 4 | 4 | 4 | 4 | 4 | 4 | 4 | 4 | 4 | 4 |
| Untreated | 0 | 0 | 0 | 0 | 0 | | 0 | 0 | 0 | | 0 | 0 | 0 | 0 | 0 | 0 | 0 | 0 |
| Comparison 5-tert-butyl-3-(2,4-dichloro-5-isopropoxyphenyl)-1,3,4-oxadiazol-2-one | 0 | 0 | 0 | 1 | 2 | | 4 | 0 | 0 | | 1 | 1 | 3 | 1 | 0 | 3 | 2 | 3 |

Test Example B

In a greenhouse, the noted plant species were treated post-emergently with the noted compounds, at a rate of 0.3 kg active ingredient/ha. The compounds were sprayed evenly over the plants as emulsions in 500 liters water/ha. Two weeks after the treatment, the compounds of the invention showed activity against the weeds. The comparison material did not show the same high activity.

Test Example C

In a greenhouse, the compounds noted in the table were applied at the rates mentioned. For this the formulated active ingredients were pipetted onto the water surface The test plants were treated pre-emergently and in the 1–3 leaf stage.

| Compounds | ALOMY | AGRRE | AVEFA | BROTE | SETVI | PANSS | SORHA | CYPES | ABUTH | GALAP | CPOSS | MATCH | POLSS | SEBEX | SOLSS | VERPE | VIOSS |
|---|---|---|---|---|---|---|---|---|---|---|---|---|---|---|---|---|---|
| Ex. 1.0 | 2 | 2 | 2 | — | 4 | 3 | 3 | — | 4 | 3 | 4 | 4 | 4 | 4 | 4 | 4 | 3 |
| Ex. 1.1 | 3 | 3 | 3 | — | 4 | 3 | 3 | — | 4 | 3 | 3 | 4 | 4 | 4 | 4 | 4 | 3 |
| Ex. 1.2 | 4 | — | 3 | — | 3 | — | 3 | 3 | 4 | 3 | 4 | 4 | 4 | 4 | 4 | 4 | 4 |
| Ex. 1.6 | 4 | 3 | 3 | 2 | 4 | 3 | 3 | 3 | 4 | 3 | 4 | 4 | 4 | 4 | 4 | 4 | 4 |
| Ex. 1.7 | 3 | 3 | 2 | — | 3 | 3 | 3 | — | 4 | 4 | 4 | 3 | 4 | 4 | 4 | 4 | 4 |
| Ex. 1.8 | 3 | 3 | 3 | — | 3 | 3 | 3 | 3 | 4 | 3 | 4 | 3 | 4 | 4 | 4 | 4 | 4 |
| Ex. 1.10 | — | — | 3 | — | 3 | — | 3 | — | 4 | — | 3 | 3 | 4 | 3 | 4 | 4 | 3 |
| Ex. 1.12 | — | — | — | — | 3 | 2 | 3 | — | 4 | — | 3 | 2 | 4 | 3 | 4 | 3 | 3 |
| Ex. 1.13 | 3 | 2 | 3 | — | 3 | 3 | 3 | 3 | 4 | — | 4 | 4 | 4 | 3 | 4 | 4 | 3 |
| Ex. 1.18 | 3 | 3 | 3 | 3 | 4 | 3 | 3 | 3 | 4 | 4 | 4 | 4 | 4 | 4 | 4 | 4 | 3 |
| Ex. 2.1 | 3 | 3 | 4 | 4 | 4 | 4 | 3 | 4 | 4 | 4 | 4 | 4 | 4 | 4 | 4 | 4 | 4 |
| Ex. 2.11 | 3 | 3 | 3 | — | 4 | 4 | 4 | — | 4 | 4 | 4 | 4 | 4 | 4 | 4 | 4 | 4 |
| Ex. 2.12 | 3 | — | 4 | — | 3 | 3 | 4 | 3 | 4 | 4 | 3 | 4 | 4 | 4 | 4 | 4 | 3 |
| Ex. 2.13 | 3 | — | 3 | — | 3 | — | 3 | 3 | 4 | 3 | 4 | 4 | 4 | 4 | 4 | 4 | 3 |
| Ex. 2.17 | 3 | 3 | 3 | — | 4 | 3 | 3 | 3 | 4 | 3 | 4 | 4 | 4 | 4 | 4 | 4 | 3 |
| Ex. 2.18 | 3 | — | 3 | — | 3 | 3 | 3 | 3 | 4 | 3 | 3 | 4 | 4 | 4 | 4 | 4 | 3 |
| Ex. 2.24 | 3 | — | 3 | — | 3 | 3 | 3 | 3 | 4 | 3 | 4 | 3 | 4 | 4 | 4 | 4 | 3 |
| Ex. 2.38 | — | 3 | — | — | 3 | 3 | — | — | 4 | 3 | 3 | 4 | 3 | 4 | 4 | 4 | 4 |
| Ex. 4.12 | 4 | 3 | 4 | 4 | 4 | 4 | 3 | 3 | 4 | 4 | 4 | 4 | 4 | 4 | 4 | 4 | 4 |
| Untreated | 0 | 0 | 0 | 0 | 0 | 0 | 0 | 0 | 0 | 0 | 0 | 0 | 0 | 0 | 0 | 0 | 0 |
| Comparison 5-tert-butyl-3-(2,4-dichloro-5-isopropoxyphenyl)-1,3,4-oxadiazol-2-one | 0 | 1 | 1 | 0 | 1 | 0 | 1 | 1 | 4 | 2 | 3 | 2 | 3 | 2 | 4 | 1 | 3 |

| Compound | Concentration kg/ha | ORYSA | ECHCG | CYPDI | SCPJU | MOOVA |
|---|---|---|---|---|---|---|
| Ex. 1.0 | 0.04 | 0 | 2 | 4 | 1 | 4 |
| Ex. 1.1 | 0.04 | 0 | 3 | 4 | 3 | 4 |
| Ex. 1.17 | 0.1 | 0 | — | 4 | — | 4 |
| Ex. 1.2 | 0.005 | 1 | 4 | 4 | 4 | 4 |
| Ex. 1.4 | 0.05 | 1 | 3 | 4 | 2 | 4 |
| Ex. 1.5 | 0.10 | 0 | 3 | 4 | 1 | 2 |
| Ex. 1.6 | 0.04 | 1 | 4 | 4 | 4 | 4 |
| Ex. 1.7 | 0.04 | 0 | 4 | 4 | 3 | 2 |
| Ex. 1.8 | 0.04 | 0 | 4 | 4 | 4 | 4 |
| Ex. 1.9 | 0.0125 | 0 | 3 | 4 | 3 | 4 |
| Ex. 1.10 | 0.01 | 0 | 4 | 4 | 4 | 4 |
| Ex. 1.11 | 0.05 | 1 | 4 | 4 | 4 | 4 |
| Ex. 1.13 | 0.02 | 1 | 3 | 4 | 2 | 4 |
| Ex. 1.14 | 0.02 | 0 | 4 | 4 | 2 | 4 |
| Ex. 1.15 | 0.01 | 0 | 1 | 4 | 0 | 4 |
| Ex. 1.18 | 0.01 | 2 | 4 | 4 | 3 | 4 |
| Ex. 1.21 | 0.025 | 1 | 4 | 4 | 3 | 4 |
| Ex. 1.22 | 0.05 | 1 | 4 | 4 | 2 | 4 |
| Ex. 1.29 | 0.2 | 0 | — | 4 | 3 | 4 |
| Ex. 1.36 | 0.04 | 1 | 4 | 4 | 3 | 4 |
| Ex. 2.0 | 0.05 | 1 | 3 | 4 | 3 | 4 |
| Ex. 2.1 | 0.01 | 1 | 4 | 4 | 4 | 4 |
| Ex. 2.17 | 0.01 | 0 | 3 | — | 1 | 4 |
| Ex. 2.18 | 0.01 | 1 | 3 | 4 | 2 | 4 |
| Ex. 2.38 | 0.04 | 0 | 3 | — | 2 | 4 |
| Ex. 3.3 | 0.08 | 1 | 4 | 4 | 4 | 4 |
| Ex. 4.100 | 0.05 | 1 | 4 | 4 | 4 | 4 |
| Ex. 4.101 | 0.05 | 1 | 4 | 3 | 3 | 4 |
| Ex. 4.102 | 0.025 | 0 | — | 4 | — | 4 |
| Ex. 4.103 | 0.01 | 0 | — | — | — | 4 |
| Ex. 4.104 | 0.1 | 1 | 4 | 4 | 3 | 4 |
| Ex. 4.105 | 0.05 | 1 | 4 | 4 | 4 | 4 |
| Ex. 4.122 | 0.04 | 1 | — | — | — | |
| Ex. 4.125 | 0.025 | 0 | 4 | 4 | 4 | — |
| Ex. 4.129 | 0.1 | 0 | 4 | 4 | 3 | 4 |
| Ex. 4.130 | 0.025 | 1 | 4 | 4 | 3 | 4 |
| Ex. 4.135 | 0.025 | 1 | 3 | 4 | 3 | 4 |
| Ex. 4.137 | 0.1 | 0 | 3 | — | — | 4 |
| Ex. 4.138 | 0.04 | 0 | — | 4 | 2 | 3 |
| Ex. 4.140 | 0.04 | 0 | 4 | 4 | 3 | 4 |
| Ex. 4.141 | 0.08 | 0 | 3 | 4 | 3 | 4 |
| Ex. 4.143 | 0.08 | 0 | 3 | 4 | 3 | 4 |
| Ex. 4.144 | 0.04 | 0 | — | 4 | — | 4 |
| Ex. 4.146 | 0.2 | 0 | 4 | 4 | 3 | 4 |
| Ex. 4.147 | 0.08 | 0 | 4 | 4 | 2 | 4 |
| Ex. 4.148 | 0.08 | 0 | 4 | 4 | 2 | 4 |
| Ex. 4.150 | 0.04 | 0 | 4 | 4 | — | 4 |
| Ex. 4.151 | 0.04 | 0 | — | 4 | — | 3 |
| Ex. 4.152 | 0.1 | 0 | 4 | 3 | 4 | 4 |
| Ex. 4.153 | 0.1 | 0 | 4 | 4 | 3 | 4 |
| Ex. 4.154 | 0.04 | 0 | 4 | 4 | 2 | 4 |
| Ex. 4.155 | 0.04 | 1 | 4 | 4 | 2 | 4 |
| Ex. 4.157 | 0.2 | 0 | 4 | 3 | 3 | 4 |
| Ex. 4.158 | 0.1 | 0 | 4 | 4 | 4 | 4 |
| Ex. 4.159 | 0.1 | 0 | 4 | 4 | 4 | 4 |
| Ex. 4.164 | 0.05 | 0 | 4 | 4 | 4 | 4 |
| Ex. 4.165 | 0.05 | 0 | 4 | 4 | 4 | 4 |
| Ex. 4.166 | 0.05 | 1 | 4 | 4 | 4 | 4 |
| Ex. 4.167 | 0.05 | 0 | 4 | 4 | 3 | 4 |
| Ex. 4.168 | 0.05 | 0 | 4 | 4 | 3 | 4 |
| Ex. 4.169 | 0.05 | 0 | 4 | 4 | 3 | 4 |
| Ex. 4.177 | 0.08 | 0 | 4 | 4 | 4 | 4 |
| Ex. 4.178 | 0.025 | 0 | 4 | 4 | 4 | 4 |
| Ex. 4.179 | 0.1 | 1 | 3 | 4 | 3 | 4 |
| Ex. 4.180 | 0.05 | 1 | 4 | 4 | 3 | 4 |
| Ex. 4.185 | 0.1 | 1 | 3 | 4 | 2 | 4 |
| Ex. 4.186 | 0.1 | 1 | 4 | — | 2 | 4 |
| Ex. 4.187 | 0.005 | — | 3 | 3 | 2 | 3 |
| Ex. 4.189 | 0.005 | 1 | 3 | 4 | 3 | 3 |
| Ex. 4.191 | 0.02 | 1 | 4 | 4 | — | 4 |
| Ex. 4.192 | 0.04 | 0 | — | 4 | — | 3 |
| Ex. 4.194 | 0.05 | 1 | — | — | 3 | 4 |
| Ex. 4.196 | 0.1 | 1 | 4 | 3 | 4 | 4 |
| Ex. 4.197 | 0.1 | 1 | 4 | 4 | 4 | 4 |

-continued

| Compound | Concentration kg/ha | ORYSA | ECHCG | CYPDI | SCPJU | MOOVA |
|---|---|---|---|---|---|---|
| Ex. 4.198 | 0.1 | 0 | 3 | — | — | 4 |
| Ex. 4.2 | 0.025 | 0 | 4 | — | 4 | 4 |
| Ex. 4.200 | 0.01 | 1 | 3 | — | — | 4 |
| Ex. 4.205 | 0.025 | 1 | 4 | — | 4 | 4 |
| Ex. 4.206 | 0.04 | 0 | 3 | 4 | 2 | 4 |
| Ex. 4.228 | 0.08 | 0 | 4 | 4 | 3 | 4 |
| Ex. 4.230 | 0.08 | 1 | 3 | 4 | 2 | 4 |
| Ex. 4.234 | 0.04 | 0 | 4 | 4 | 3 | 4 |
| Ex. 4.26 | 0.025 | 0 | 4 | 4 | 3 | 4 |
| Ex. 4.27 | 0.01 | 1 | 4 | 4 | 2 | 4 |
| Ex. 4.227 | 0.1 | 1 | 3 | 2 | 3 | 4 |
| Ex. 4.229 | 0.05 | 1 | 4 | — | 4 | 4 |
| Ex. 4.231 | 0.1 | 0 | 3 | — | — | 4 |
| Ex. 4.233 | 0.08 | 0 | 4 | 4 | 3 | 4 |
| Ex. 4.235 | 0.02 | 1 | 3 | 4 | — | 4 |
| Ex. 4.236 | 0.2 | 0 | 4 | 4 | 2 | 4 |
| Ex. 4.237 | 0.04 | 0 | 3 | 4 | 3 | 4 |
| Ex. 4.238 | 0.04 | 0 | 4 | 4 | 3 | 4 |
| Ex. 4.239 | 0.04 | 0 | 4 | 4 | 4 | 4 |
| Ex. 4.240 | 0.08 | 1 | 3 | 4 | 2 | 4 |
| Ex. 4.241 | 0.04 | 0 | 3 | 4 | 2 | 4 |
| Ex. 4.242 | 0.04 | 0 | — | 4 | — | 3 |
| Ex. 4.243 | 0.08 | 0 | 2 | 4 | 2 | 4 |
| Ex. 4.244 | 0.08 | 0 | 4 | 4 | 3 | 4 |
| Ex. 4.245 | 0.08 | 0 | 3 | 4 | 2 | 4 |
| Ex. 4.246 | 0.1 | 0 | 4 | 4 | — | 4 |
| Ex. 4.247 | 0.1 | 0 | 4 | 4 | 3 | 4 |
| Ex. 4.248 | 0.025 | 0 | 3 | 4 | 2 | 4 |
| Ex. 4.25 | 0.05 | 1 | 4 | 4 | 3 | 4 |
| Ex. 4.251 | 0.1 | 1 | 3 | — | 4 | 4 |
| Ex. 4.252 | 0.05 | 0 | — | 3 | — | — |
| Ex. 4.255 | 0.1 | 0 | — | — | — | 4 |
| Ex. 4.257 | 0.1 | 0 | 3 | 3 | — | 4 |
| Ex. 4.275 | 0.025 | 0 | 4 | — | 3 | 4 |
| Ex. 4.276 | 0.005 | 1 | 4 | 4 | 3 | 4 |
| Ex. 4.277 | 0.005 | 1 | — | 3 | — | 3 |
| Ex. 4.280 | 0.1 | 1 | — | 3 | — | 4 |
| Ex. 4.281 | 0.025 | 1 | 3 | — | 2 | 4 |
| Ex. 4.288 | 0.2 | 0 | — | 4 | — | 4 |
| Ex. 4.29 | 0.05 | 1 | 4 | 4 | 4 | 4 |
| Ex. 4.290 | 0.1 | 0 | 3 | 4 | 2 | 4 |
| Ex. 4.291 | 0.025 | 1 | 4 | 4 | 3 | 4 |
| Ex. 4.292 | 0.1 | 0 | 4 | 4 | 3 | 4 |
| Ex. 4.295 | 0.2 | 0 | 3 | — | 4 | 4 |
| Ex. 4.31 | 0.1 | 0 | 3 | 4 | 3 | 4 |
| Ex. 4.32 | 0.005 | 1 | 3 | 4 | 2 | 4 |
| Ex. 4.33 | 0.005 | 1 | — | — | — | 4 |
| Ex. 4.34 | 0.002 | 1 | 3 | 4 | 2 | 4 |
| Ex. 4.35 | 0.005 | 1 | 4 | 4 | 4 | 4 |
| Ex. 4.37 | 0.01 | 0 | 3 | 2 | 2 | 4 |
| Ex. 4.38 | 0.025 | 1 | — | — | — | 4 |
| Ex. 4.41 | 0.005 | 1 | 3 | 4 | — | 4 |
| Ex. 4.42 | 0.02 | 1 | 4 | 4 | 3 | 4 |
| Ex. 4.43 | 0.02 | 1 | 4 | 3 | 2 | 4 |
| Ex. 4.49 | 0.25 | 1 | — | 3 | — | 4 |
| Ex. 4.50 | 0.02 | 1 | 3 | 4 | 2 | 4 |
| Ex. 4.56 | 0.1 | 1 | 3 | 4 | 2 | 4 |
| Ex. 4.57 | 0.025 | 1 | 4 | — | 3 | 4 |
| Ex. 4.58 | 0.05 | 0 | 4 | 4 | 3 | 4 |
| Ex. 4.59 | 0.04 | 0 | 4 | 4 | 4 | 4 |
| Ex. 4.60 | 0.1 | 0 | 4 | 4 | 4 | 4 |
| Ex. 4.61 | 0.02 | 0 | 4 | 4 | 2 | 4 |
| Ex. 4.62 | 0.04 | 0 | 4 | 4 | 2 | 4 |
| Ex. 4.64 | 0.04 | 0 | 4 | 4 | 2 | 4 |
| Ex. 4.65 | 0.005 | 0 | 3 | 4 | 3 | 4 |
| Ex. 4.66 | 0.1 | 0 | — | — | — | 4 |
| Ex. 4.67 | 0.1 | 0 | — | — | — | 4 |
| Ex. 4.68 | 0.04 | 0 | 4 | 4 | 2 | 4 |
| Ex. 4.69 | 0.01 | 0 | 4 | 4 | 2 | 4 |
| Ex. 4.70 | 0.08 | 0 | 4 | 4 | 4 | 4 |
| Ex. 4.71 | 0.08 | 0 | 3 | 4 | 3 | 4 |
| Ex. 4.73 | 0.05 | 0 | 4 | 4 | 4 | 4 |
| Ex. 4.74 | 0.08 | 0 | 4 | 4 | 3 | 4 |
| Ex. 4.75 | 0.05 | 0 | 4 | 4 | 4 | 4 |

-continued

| Compound | Concentration kg/ha | ORYSA | ECHCG | CYPDI | SCPJU | MOOVA |
|---|---|---|---|---|---|---|
| Ex. 4.76 | 0.04 | 0 | 3 | 4 | 2 | 4 |
| Ex. 4.79 | 0.04 | 0 | 3 | — | — | 4 |
| Ex. 4.80 | 0.04 | 1 | 4 | — | 3 | 4 |
| Ex. 4.82 | 0.1 | 0 | — | — | — | 4 |
| Ex. 4.83 | 0.1 | 0 | 4 | 4 | 4 | 4 |
| Ex. 4.84 | 0.02 | 1 | 3 | 4 | 3 | 4 |
| Ex. 4.85 | 0.025 | 0 | 4 | 4 | 3 | 4 |
| Ex. 4.87 | 0.1 | 0 | 4 | 4 | 4 | 4 |
| Ex. 4.88 | 0.1 | 0 | 4 | 4 | 2 | 4 |
| Ex. 4.89 | 0.1 | 0 | — | 3 | — | 4 |
| Ex. 4.90 | 0.025 | 0 | 3 | — | — | 4 |
| Ex. 4.91 | 0.1 | 0 | 4 | 4 | 3 | 4 |
| Ex. 4.92 | 0.05 | 1 | 4 | 4 | 4 | 4 |
| Ex. 4.93 | 0.025 | 0 | 4 | 4 | 2 | 4 |
| Ex. 4.94 | 0.1 | 0 | — | — | 3 | 4 |
| Ex. 4.95 | 0.025 | 1 | 4 | 3 | 3 | 4 |
| Ex. 4.96 | 0.005 | 0 | 3 | 4 | 2 | 4 |
| Ex. 4.97 | 0.1 | 0 | 4 | 4 | 4 | 4 |
| Ex. 4.98 | 0.05 | 1 | 4 | 4 | 3 | 4 |
| Ex. 4.99 | 0.025 | 1 | 4 | 4 | 3 | 4 |
| Untreated | | 0 | 0 | 0 | 0 | 0 |

As the table shows, the compounds of the invention show good activity against *Echinochloa crus-galli* (ECHGH) *Cyperus difformis* (CYPDI), *Scirpus juncoides* (SCPJU) and *Monochoria vaginalis* (MOOVA).

Example D

In a greenhouse, the noted plant species were treated with the noted compounds, at a rate of 0.03 kg active ingredient/ha. The compounds were sprayed evenly over the plants as emulsions in 500 liters water/ha. Two weeks after the treatment, the compounds of the invention showed excellent activity against the weeds. The comparison material did not show the same high activity.

| Compound | ALOMY | SETVI | PANSS | ABUTH | GALAP | IPOSS | MATCH | POLSS | SEBEX | SOLSS | VERPE | VIOSS |
|---|---|---|---|---|---|---|---|---|---|---|---|---|
| Ex. 3.1 | 3 | 4 | 4 | 4 | 3 | 4 | 4 | 4 | 4 | 4 | 4 | 4 |
| Untreated | 0 | 0 | 0 | 0 | 0 | 0 | 0 | 0 | 0 | 0 | 0 | 0 |
| Comparison 5-tert.-Butyl-3-(2,4-dichloro isopropoxyphenyl)-1,3,4-oxadiazol-2-one | 1 | 2 | 1 | 3 | 2 | 3 | 2 | 3 | 2 | 4 | 2 | 2 |

Example E

In a greenhouse, the noted plant species were treated with the noted compounds, at a rate of 0.1 kg active ingredient/ha. The compounds were sprayed evenly over the plants as emulsions in 500 liters water/ha. Two weeks after the treatment, the compounds of the invention showed excellent activity against the weeds. The comparison material did not show the same high activity.

| Compound | ALOMY | AGRRE | AVEFA | BROTE | SETVI | PANSS | SORHA | CYPES | ABUTH | GALAP | IPOSS | MATCH | POLSS | SEBEX | SOLSS | VERPE | VIOSS |
|---|---|---|---|---|---|---|---|---|---|---|---|---|---|---|---|---|---|
| Ex. 4.2 | — | — | — | — | 3 | 3 | 3 | — | 4 | 3 | 3 | 4 | 4 | — | 4 | 4 | 4 |
| Ex. 4.3 | 3 | — | 3 | 3 | 4 | 4 | 3 | — | 4 | 4 | 4 | 4 | 4 | 4 | 4 | 4 | 3 |

-continued

| Compound | ALOMY | AGRRE | AVEFA | BROTE | SETVI | PANSS | SORHA | CYPES | ABUTH | GALAP | IPOSS | MATCH | POLSS | SEBEX | SOLSS | VERPE | VIOSS |
|---|---|---|---|---|---|---|---|---|---|---|---|---|---|---|---|---|---|
| Ex. 4.4 | 4 | 3 | 3 | 3 | 4 | 4 | 3 | 3 | 4 | 4 | 4 | 4 | 4 | 4 | 4 | 4 | 3 |
| Untreated | 0 | 0 | 0 | 0 | 0 | 0 | 0 | 0 | 0 | 0 | 0 | 0 | 0 | 0 | 0 | 0 | 0 |
| Comparison 5-tert.-Butyl-3-(2,4-dichloro-5-isopropoxyphenyl)-3,4-oxadiazol-2-one | 1 | 1 | 0 | 0 | 2 | 2 | 1 | 0 | 4 | 2 | 3 | 2 | 3 | 4 | 3 | 2 | 2 |

What is claimed is:

1. Substituted pyrazolyl derivatives of the general formula

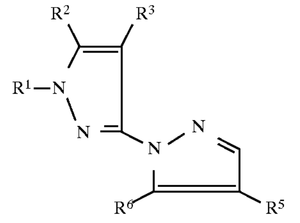

in which $R^1$ is $C_1$–$C_4$-alkyl, $R^2$ is $C_1$–$C_4$-alkyl, $C_1$–$C_4$-alkylthio, $C_1$–$C_4$-alkoxy, each of which is optionally substituted by one or more halogen atoms, $R^3$ is hydrogen or halogen, $R^5$ is hydrogen, nitro, cyano, —COOR$^7$, —C(═X)NR$^8$R$^9$ or —C(═X)R$^{10}$, $R^6$ is

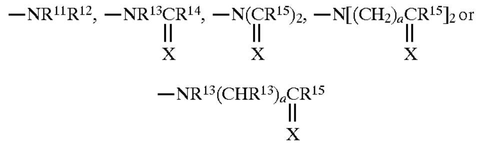

$R^7$, $R^8$ and $R^9$, which may be the same or different, are hydrogen or $C_1$–$C_4$-alkyl or $R^8$ and $R^9$ together with the nitrogen to which they are attached form a 5 or 6 membered saturated ring, $R^{10}$ is hydrogen or $C_1$–$C_4$-alkyl, optionally substituted by one or more halogen atoms, $R^{11}$ is hydrogen, $C_1$–$C_4$-alkyl, $C_2$–$C_6$-alkenyl, $C_3$–$C_6$-alkynyl or phenyl (each of which is optionally substituted by one or more halogen atoms), $C_3$–$C_8$-cycloalkyl, cyanomethyl or the group $R^{21}$CO—, $R^{12}$ is $C_1$–$C_6$-alkyl, $C_2$–$C_6$-alkenyl, $C_3$–$C_6$-alkynyl or phenyl (each of which is optionally substituted by one or more halogen atoms), $C_3$–$C_8$-cycloalkyl, cyanomethyl, $C_1$–$C_4$-alkoxy-$C_1$–$C_6$-alkyl, di-$C_1$–$C_4$-alkylamino-$C_1$–$C_4$-alkyl, tetrahydrofurylmethyl, $C_3$–$C_6$-alkynyloxy-$C_1$–$C_4$-alkyl, benzyl (optionally substituted by one or more halogen, nitro, cyano, $C_1$–$C_4$-alkyl, $C_1$–$C_4$-alkoxy or halo-$C_1$–$C_4$-alkyl groups), —C(═X) $R^{21}$, —$(CH_2)_a$—$(O)_d$-$R^{28}$, —$(CH_2)_a$—O—$(CH_2)_b$-$R^{28}$ or —$(CH_2)_a$—X-$R^{34}$ or $R^{11}$ and $R^{12}$ together with the nitrogen to which they are attached form a 3, 5 or 6 membered saturated carbocyclic or aromatic ring, in which a carbon atom is optionally substituted by an oxygen atom, $R^{13}$ is hydrogen, $C_1$–$C_4$-alkyl, $C_2$–$C_6$-alkenyl or $C_3$–$C_6$-alkynyl; or $R^{13}$ and $R^{14}$ together form the group —$(CH_2)_p$—;

$R^{14}$ and $R^{15}$, which may be the same or different, are $C_1$–$C_4$-alkyl, $C_2$–$C_6$-alkenyl, $C_3$–$C_6$-alkynyl or phenyl (each of which is optionally substituted by one or more halogen atoms), hydrogen, $C_3$–$C_6$-cycloalkyl or the groups —XR$^{18}$ or —NR$^{19}$R$^{20}$;

$R^{18}$ is $C_1$–$C_4$-alkyl, optionally substituted by one or more halogens;

$R^{19}$ and $R^{20}$, which may be the same or different, are hydrogen or $C_1$–$C_4$-alkyl;

$R^{21}$ is $C_1$–$C_4$-alkoxy-$C_1$–$C_4$-alkyl, $C_1$–$C_4$-alkylthio-$C_1$–$C_4$-alkyl, phenyl (substituted by one or more halogen, nitro, cyano, $C_1$–$C_4$-alkyl, $C_1$–$C_4$-alkoxy or halo-$C_1$–$C_4$-alkyl groups), —NR$^{31}$R$^{32}$ or —$(CH_2)_a$—$(O)_d$-$R^{33}$, $R^{28}$ is hydrogen, hydroxy, halogen, $C_1$–$C_4$-alkyl (optionally substituted by one or more $C_1$–$C_4$-alkoxy groups), $C_3$–$C_6$-cycloalkyl (optionally interrupted by one or more oxygen atoms and optionally substituted by dimethyl), furyl, thienyl or —C(═O)R$^{29}$, $R^{29}$ is $C_1$–$C_4$-alkyl or $C_1$–$C_4$-alkoxy, $R^{31}$ and $R^{32}$, which may be of the same or different, are $C_1$–$C_4$-alkyl or phenyl, $R^{33}$ is $C_3$–$C_6$-cycloalkyl (optionally interrupted by one or more oxygen atoms and optionally substituted by dimethyl), —C(═O)R$^{29}$, furyl or thienyl, $R^{34}$ is $C_1$–$C_4$-alkyl, a and b are 1, 2 or 3, d is 0 or 1, X is oxygen or sulfur, and p is 2 or 3.

2. A substituted pyrazole derivative according to claim 1 in which $R^3$ is halogen.

3. A substituted pyrazole derivative according to claim 2 in which $R^3$ is chloro.

4. A substituted pyrazole derivative according to claim 3 in which $R^5$ is hydrogen, nitro or cyano.

5. A substituted pyrazole derivative according to claim 4 in which $R^2$ is halogen substituted alkoxy.

6. A substituted pyrazole derivative according to claim 5 in which $R^1$ is methyl and $R^2$ difluoromethoxy.

7. A substituted pyrazole derivative according to claim 6 in which $R^6$ is —NHR$^{12}$ or NHCOR$^{14}$, $R^{12}$ is alkyl and $R^{14}$ is halogen substituted alkyl.

8. A herbicidal composition which comprises a compound according to claim 1 in admixture with an agriculturally acceptable carrier.

9. A herbicidal composition which comprises a compound according to claim 2 in admixture with an agriculturally acceptable carrier.

10. A herbicidal composition which comprises a compound according to claim 3 in admixture with an agriculturally acceptable carrier.

11. A herbicidal composition which comprises a compound according to claim 4 in admixture with an agriculturally acceptable carrier.

12. A herbicidal composition which comprises a compound according to claim 5 in admixture with an agriculturally acceptable carrier.

13. A herbicidal composition which comprises a compound according to claim 6 in admixture with an agriculturally acceptable carrier.

14. A herbicidal composition which comprises a compound according to claim 7 in admixture with an agriculturally acceptable carrier.

15. A method of combating weeds which comprises applying to the weeds or their locus a compound according to claim 1.

16. A method of combating weeds which comprises applying to the weeds or their locus a compound according to claim 2.

17. A method of combating weeds which comprises applying to the weeds or their locus a compound according to claim 3.

18. A method of combating weeds which comprises applying to the weeds or their locus a compound according to claim 4.

19. A method of combating weeds which comprises applying to the weeds or their locus a compound according to claim 5.

20. A method of combating weeds which comprises applying to the weeds or their locus a compound according to claim 6.

21. A method of combating weeds which comprises applying to the weeds or their locus a compound according to claim 7.

* * * * *